(12) United States Patent
Romley

(10) Patent No.: US 11,607,215 B2
(45) Date of Patent: *Mar. 21, 2023

(54) METHODS AND DEVICES FOR MANIPULATING AND FASTENING TISSUE

(71) Applicant: EndoGastric Solutions, Inc., Redmond, WA (US)

(72) Inventor: Richard Romley, Redmond, WA (US)

(73) Assignee: EndoGastric Solutions, Inc., Redmond, WA (US)

( * ) Notice: Subject to any disclaimer, the term of this patent is extended or adjusted under 35 U.S.C. 154(b) by 434 days.

This patent is subject to a terminal disclaimer.

(21) Appl. No.: 16/821,897

(22) Filed: Mar. 17, 2020

(65) Prior Publication Data

US 2020/0268376 A1 Aug. 27, 2020

Related U.S. Application Data

(62) Division of application No. 15/861,785, filed on Jan. 4, 2018, now Pat. No. 10,595,860, which is a division
(Continued)

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/00234* (2013.01); *A61B 17/072* (2013.01); *A61B 17/0218* (2013.01); *A61B 17/0644* (2013.01); *A61B 2017/00296* (2013.01); *A61B 2017/00349* (2013.01); *A61B 2017/00371* (2013.01); *A61B 2017/00473* (2013.01); *A61B 2017/00557* (2013.01); *A61B 2017/00818* (2013.01); *A61B 2017/00827* (2013.01); *A61B 2017/0645* (2013.01); *A61B 2017/0648* (2013.01); *A61B 2017/0649* (2013.01); *A61B 2017/07271* (2013.01); *A61B 2017/2905* (2013.01);
(Continued)

(58) Field of Classification Search
CPC .......... A61B 17/00234; A61B 17/0218; A61B 17/0644; A61B 17/068; A61B 17/0682; A61B 17/072; A61B 17/07207; A61B 2017/00296; A61B 2017/00349; A61B 2017/00371; A61B 2017/0046; A61B 2017/00473; A61B 2017/00557; A61B 2017/00818; A61B 2017/00827; A61B 2017/0645; A61B 2017/0648; A61B 2017/0649; A61B 2017/07221; A61B 2017/07271; A61B 2017/2905; A61B 2017/306; A61B 2017/3488; A61B 2090/064
See application file for complete search history.

(56) References Cited

U.S. PATENT DOCUMENTS 9,572,571 B2 * 2/2017 Romley ................ A61F 5/0086
9,955,957 B2 * 5/2018 Romley ........... A61B 17/00234
(Continued)

*Primary Examiner* — Robert A Lynch
(74) *Attorney, Agent, or Firm* — Fulwider Patton LLP

(57) ABSTRACT

A tissue displacing and fastening device is provided for manipulating and fastening tissue together. The device includes a tissue displacing elements, which displaces tissue. A fold is formed from the displaced tissue and the tissue is fastened together to secure the fold.

8 Claims, 32 Drawing Sheets

Related U.S. Application Data of application No. 14/558,865, filed on Dec. 3, 2014, now Pat. No. 9,861,360, which is a division of application No. 13/229,061, filed on Sep. 9, 2011, now Pat. No. 8,915,929.

(51) Int. Cl.
| | | |
|---|---|---|
| *A61B 17/00* | (2006.01) | |
| *A61B 90/00* | (2016.01) | |
| *A61B 17/064* | (2006.01) | |
| *A61B 17/29* | (2006.01) | |
| *A61B 17/30* | (2006.01) | |
| *A61B 17/02* | (2006.01) | |
| *A61B 17/34* | (2006.01) | |

(52) U.S. Cl.
CPC .. *A61B 2017/306* (2013.01); *A61B 2017/3488* (2013.01); *A61B 2090/064* (2016.02)

(56) References Cited

U.S. PATENT DOCUMENTS

| | | | |
|---|---|---|---|
| 10,010,319 B2 * | 7/2018 | Romley | A61B 17/068 |
| 10,595,860 B2 * | 3/2020 | Romley | A61B 17/068 |

* cited by examiner

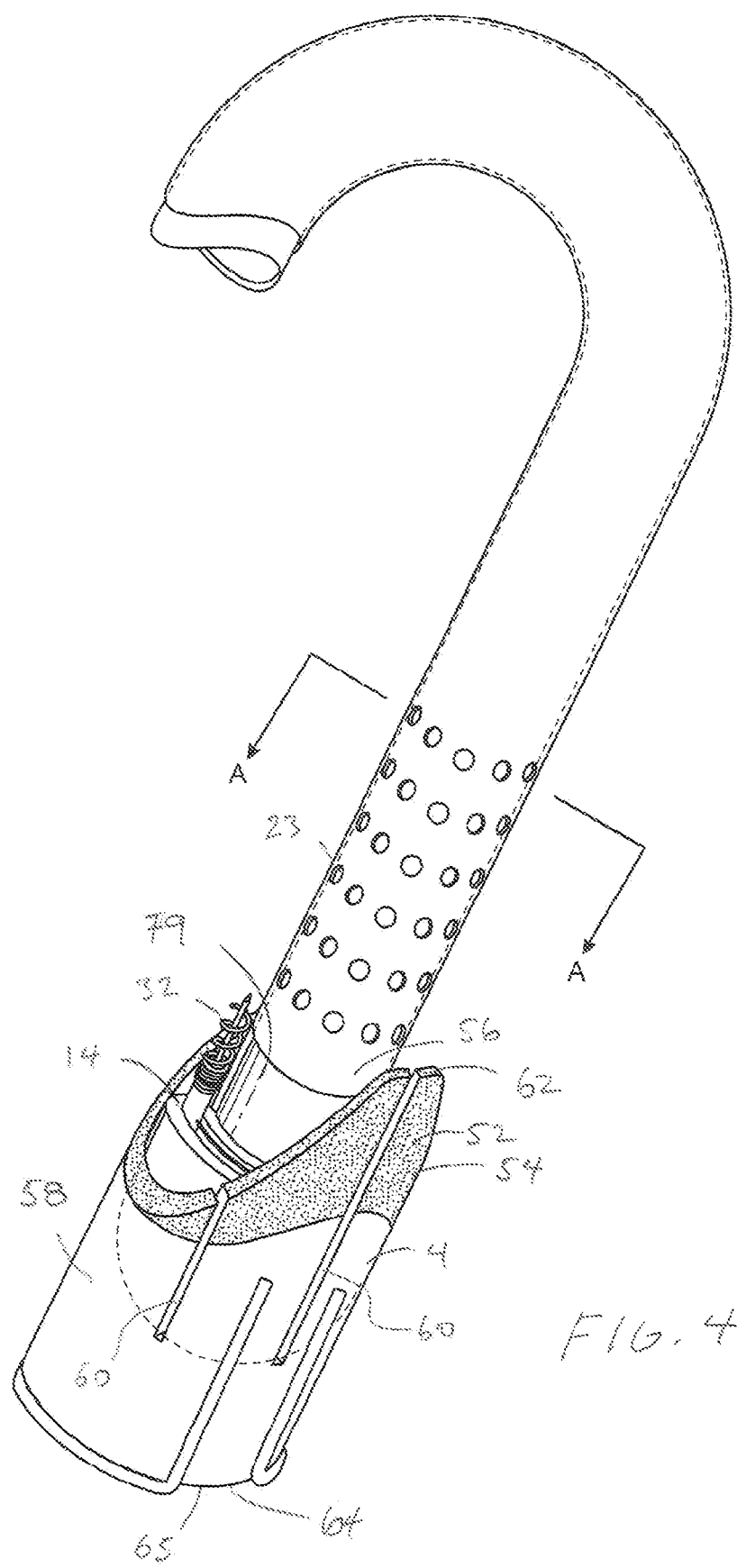

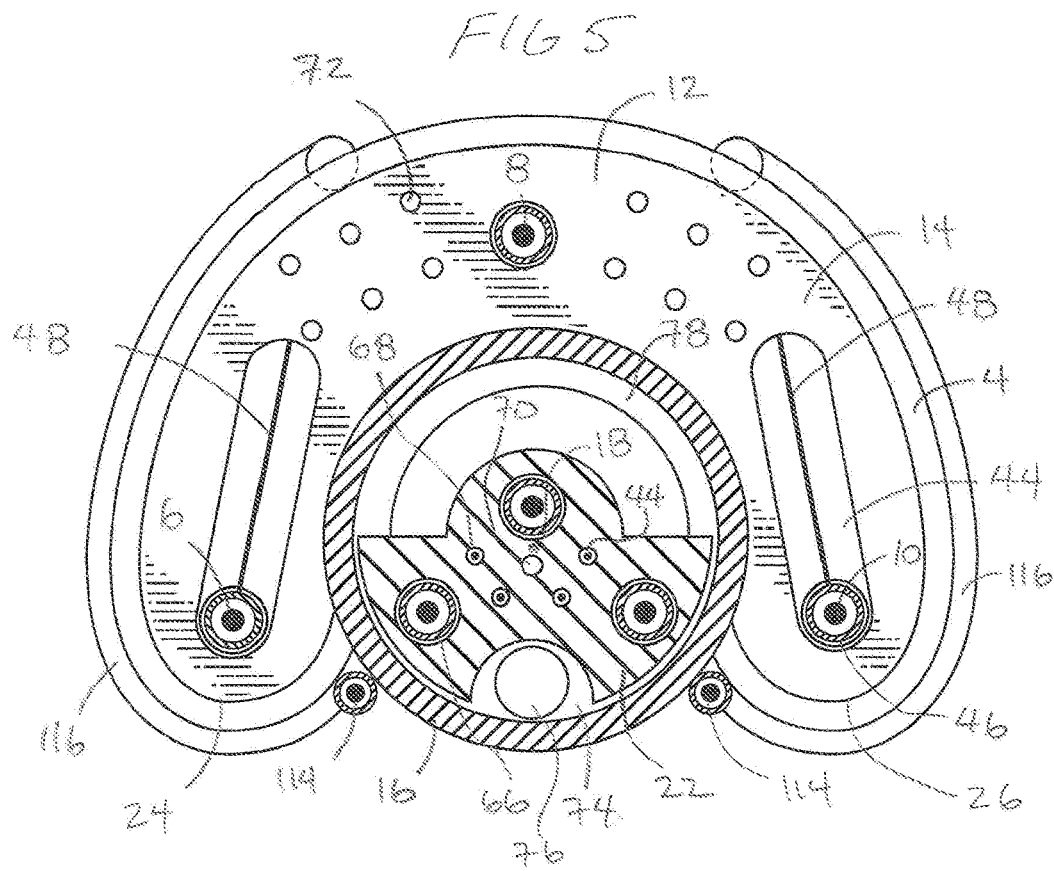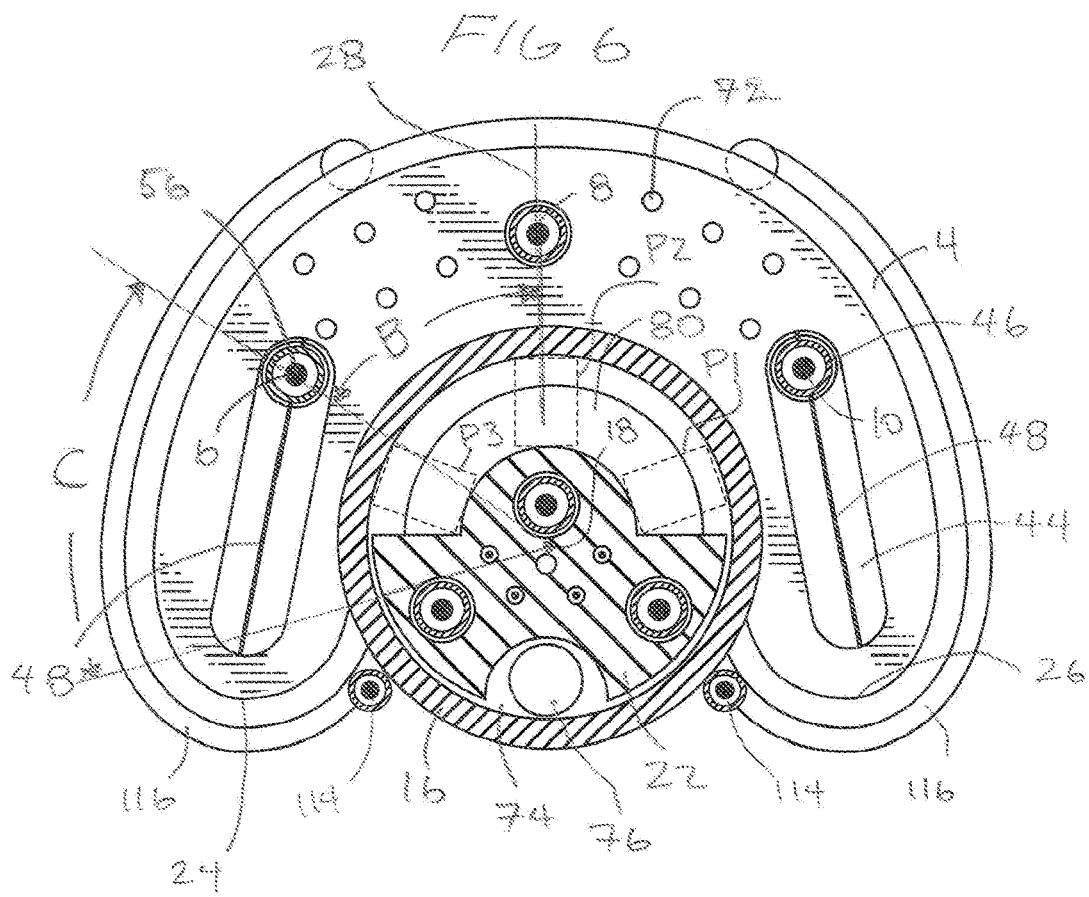

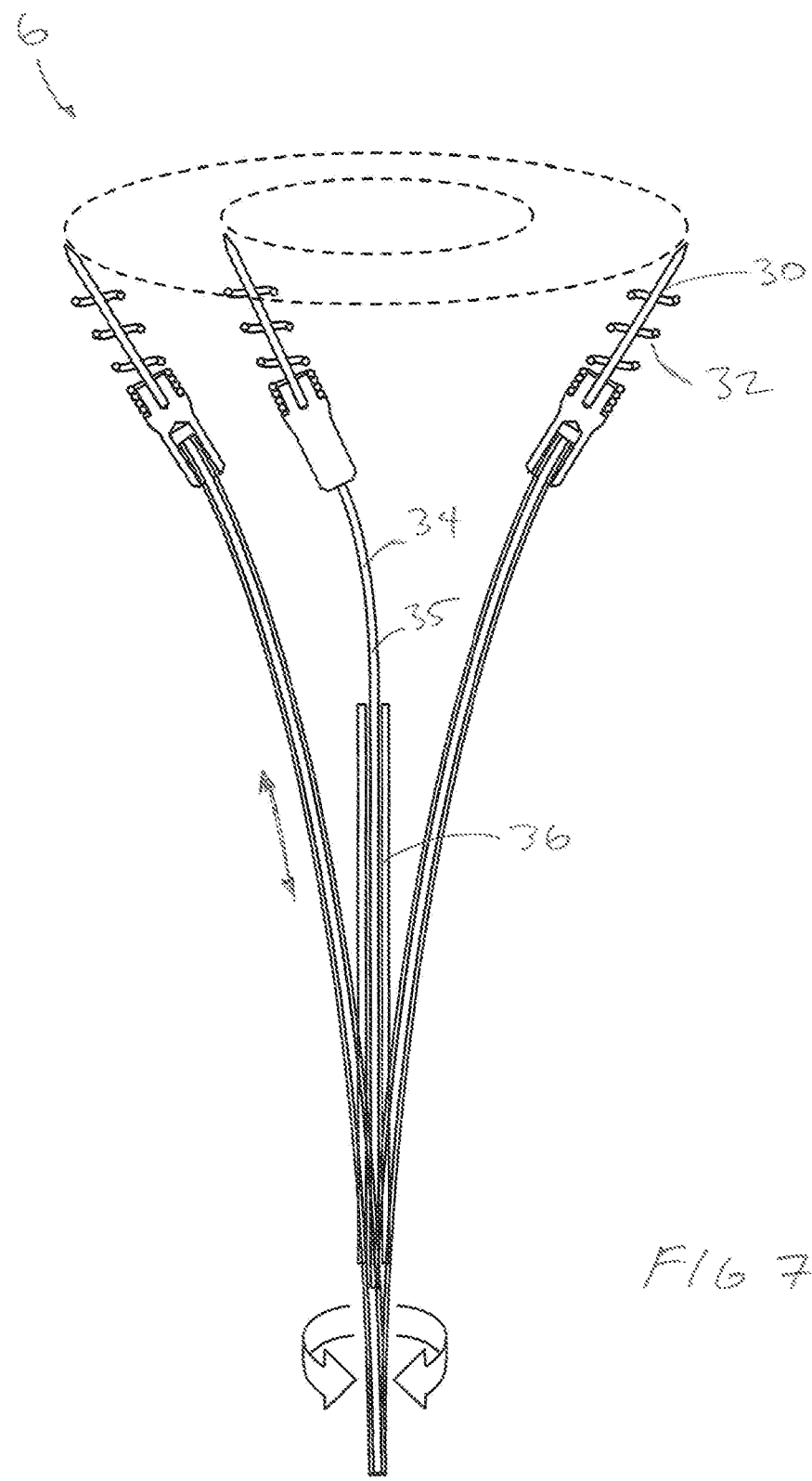

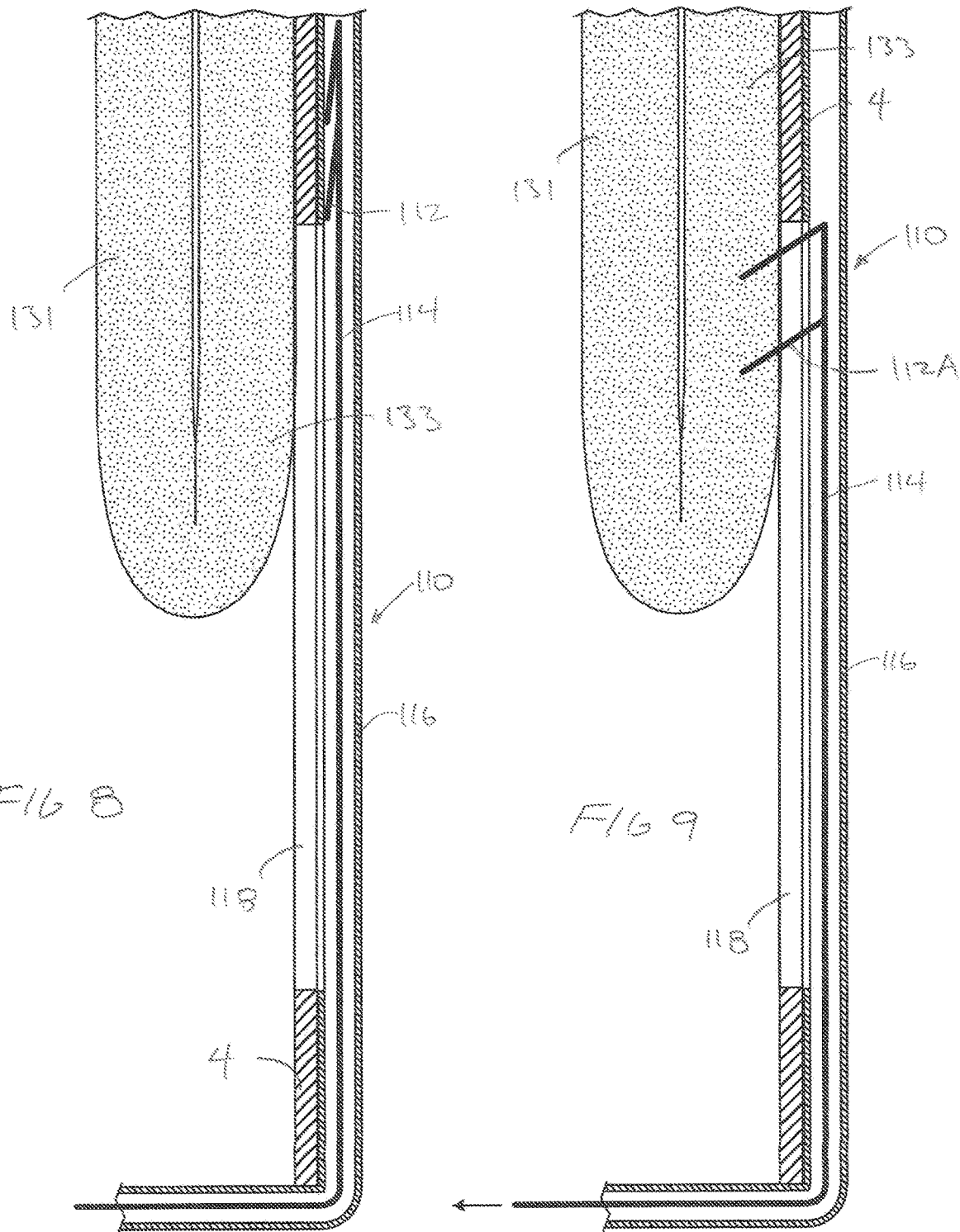

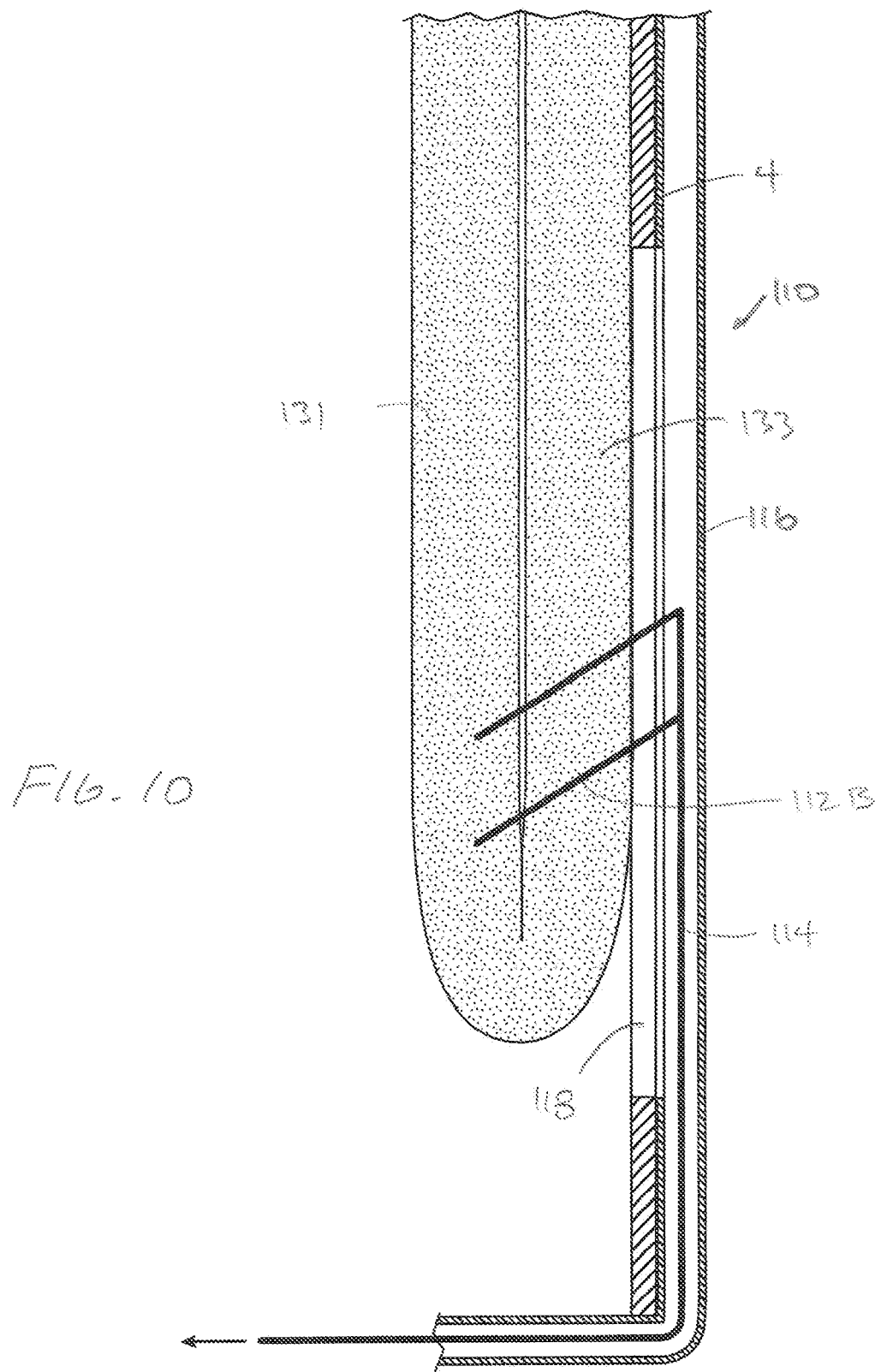

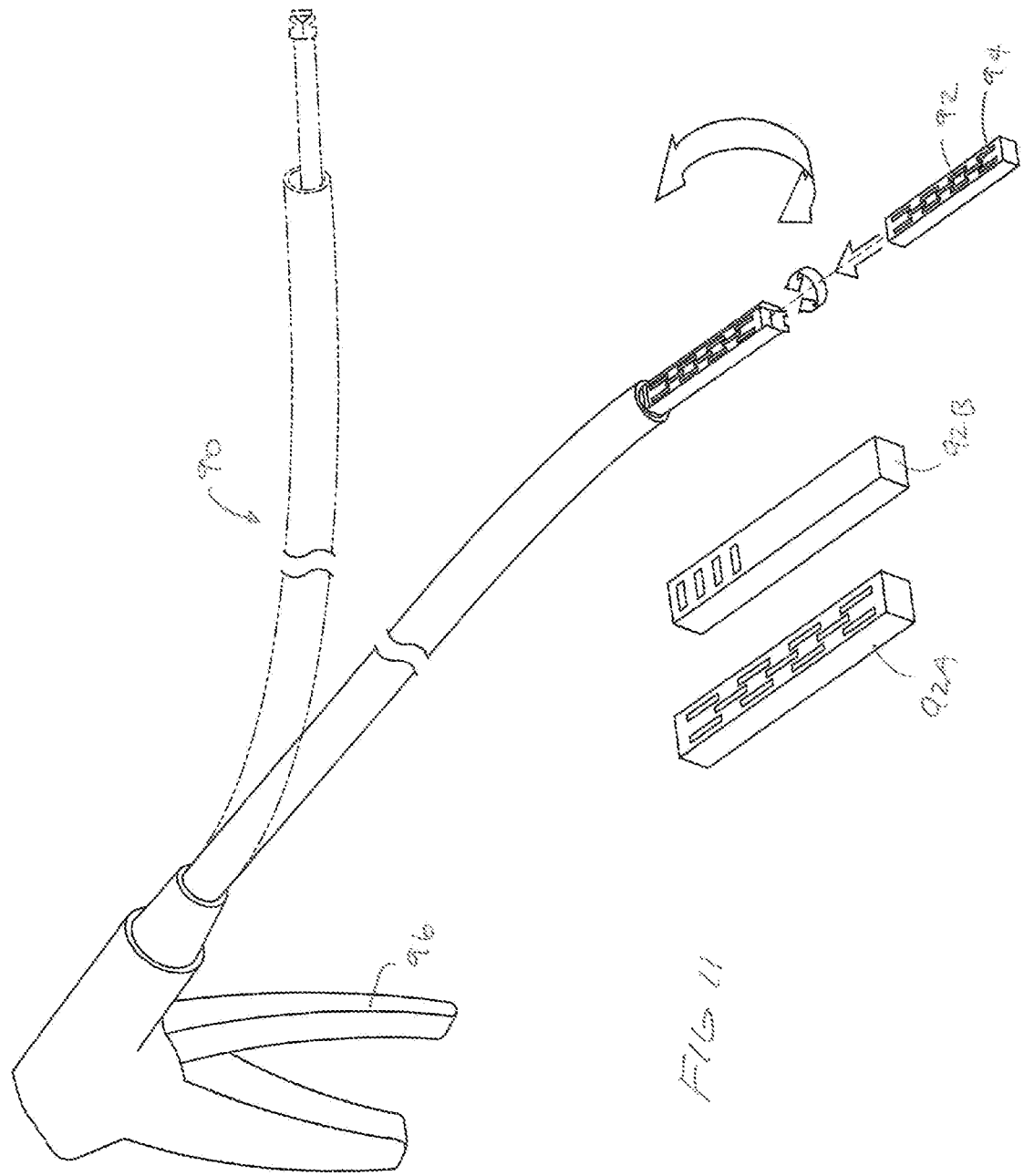

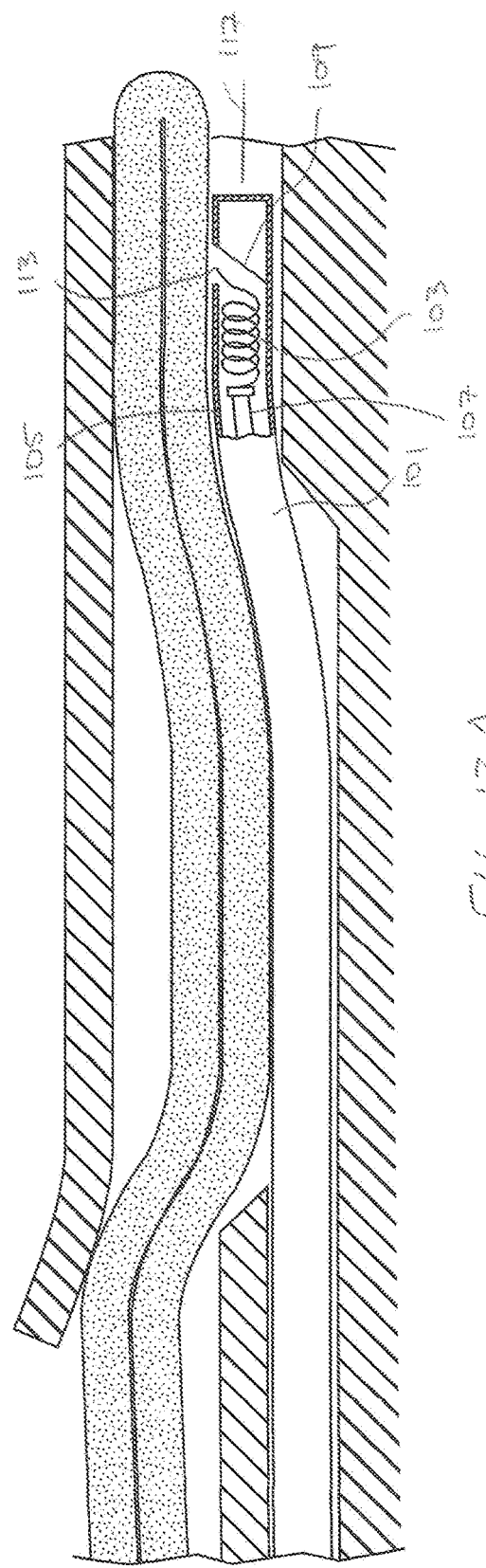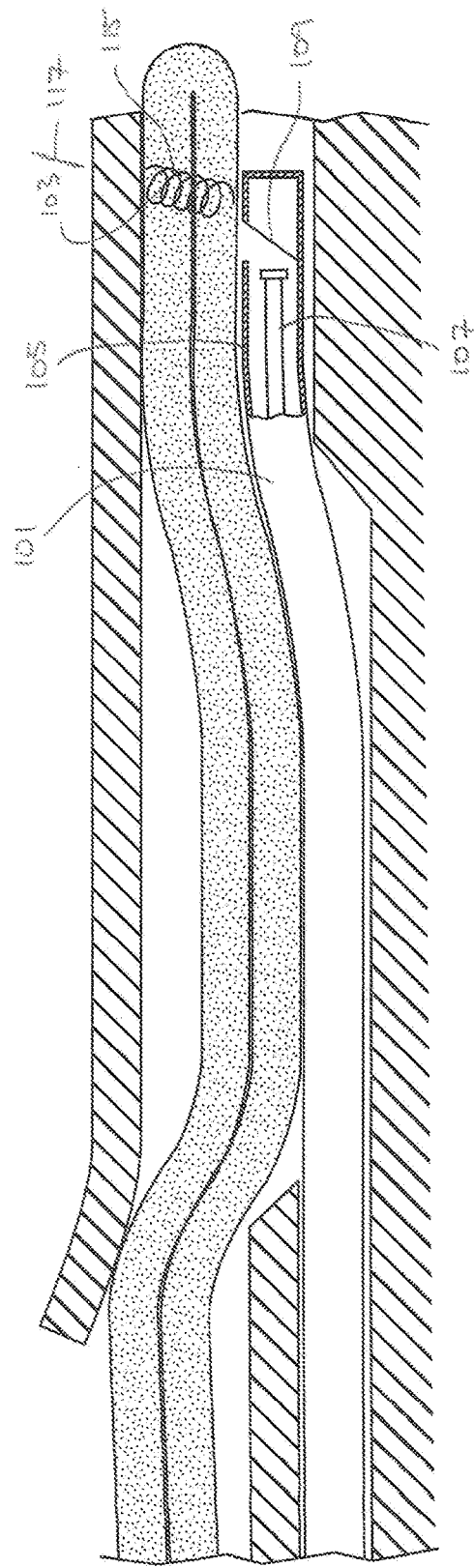

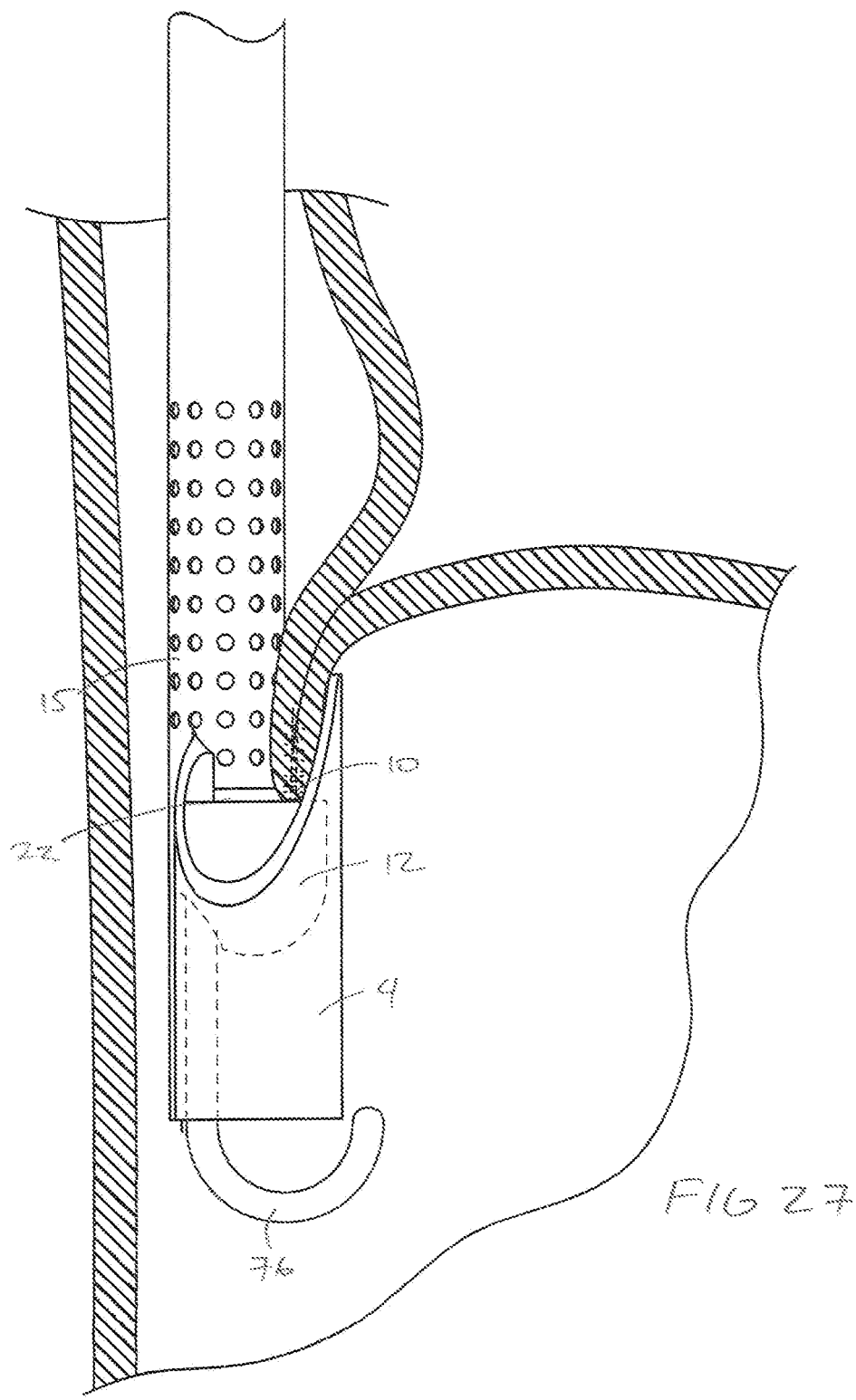

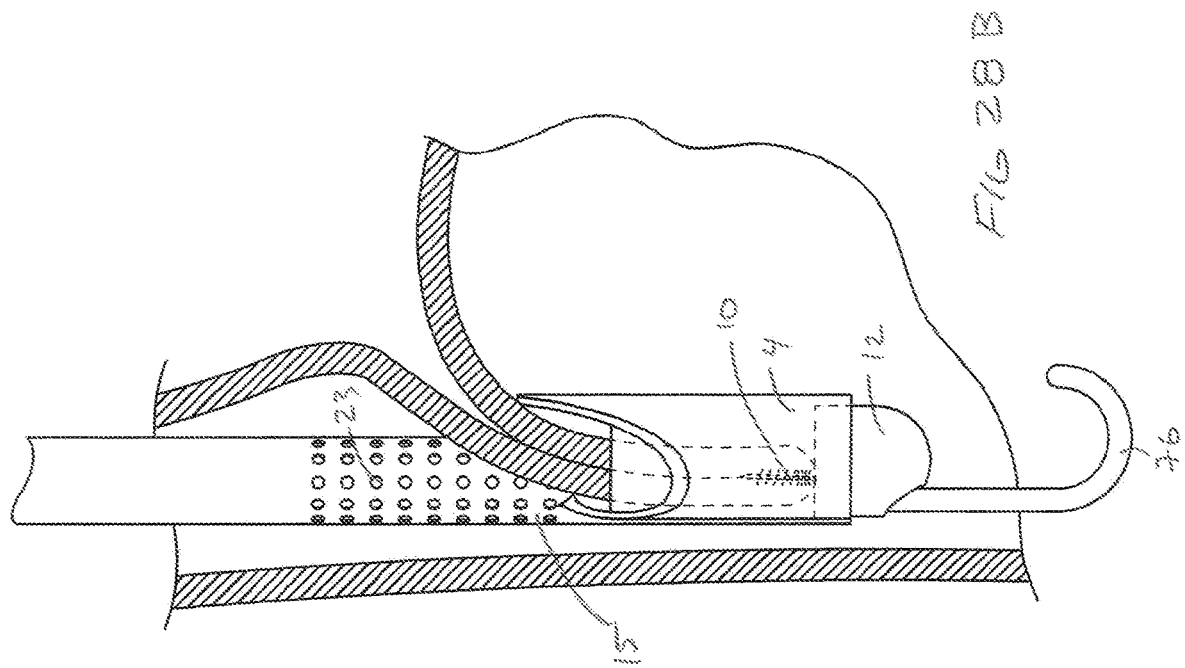
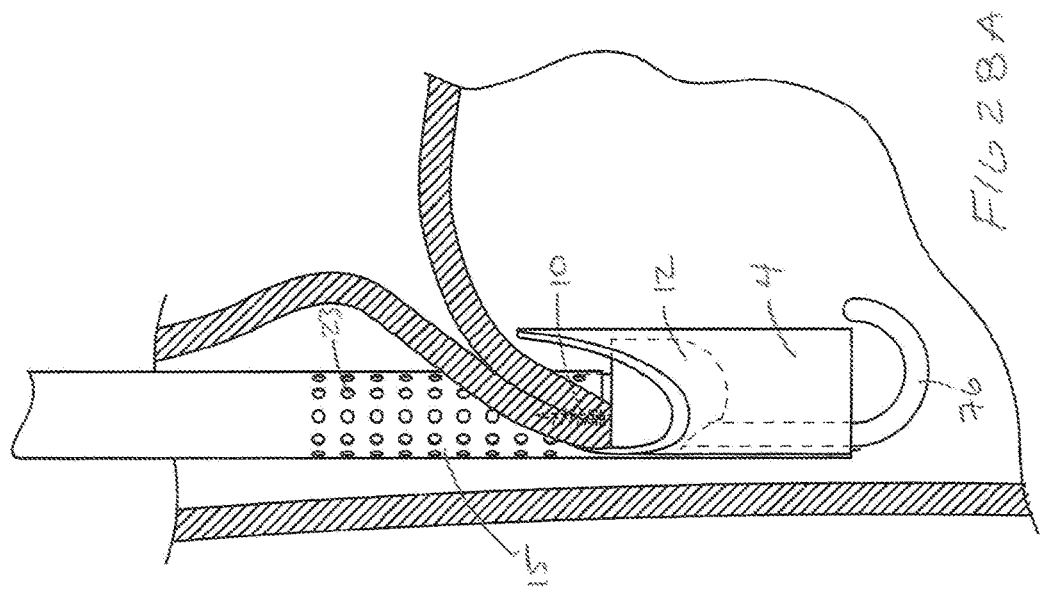

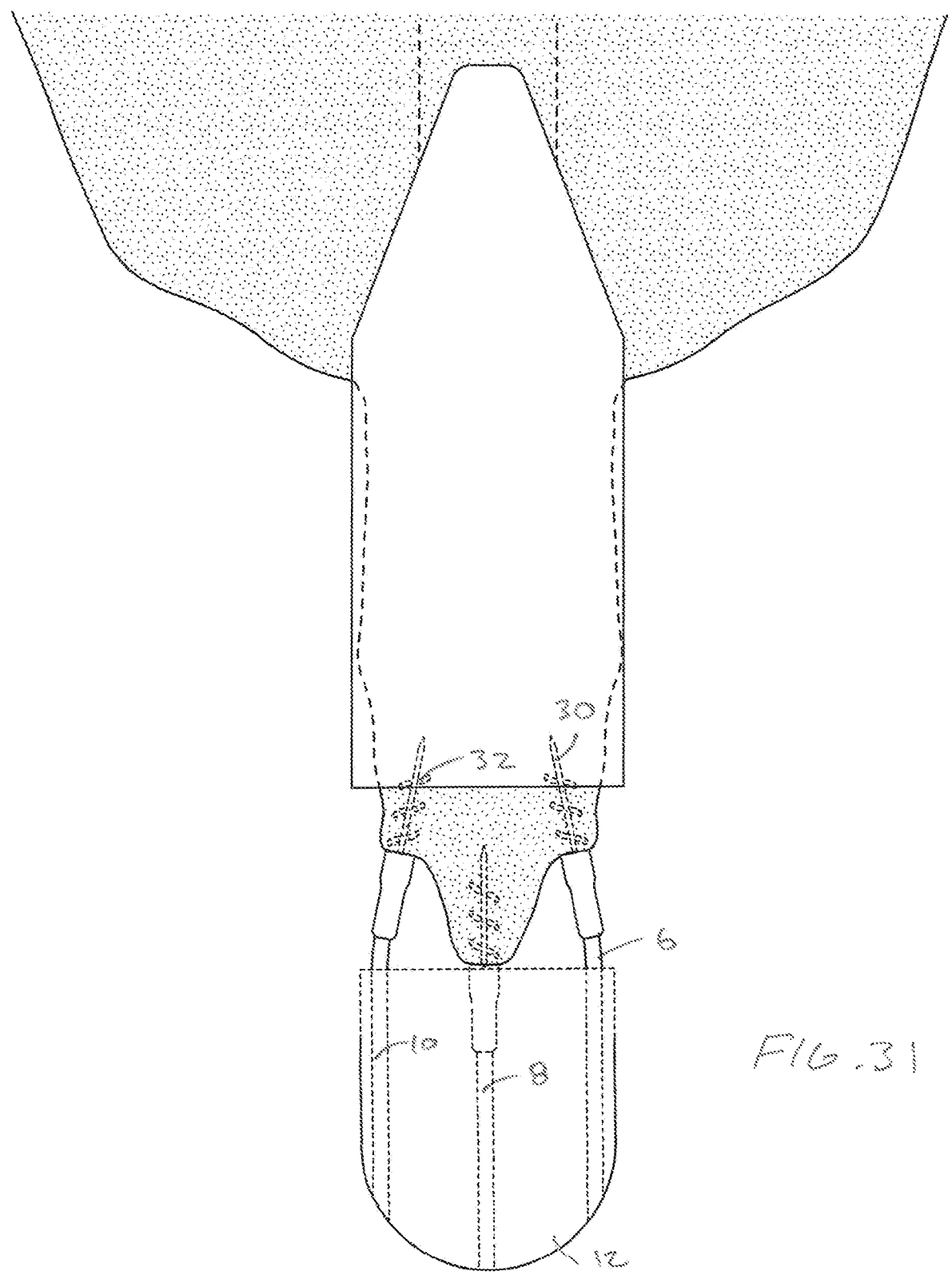

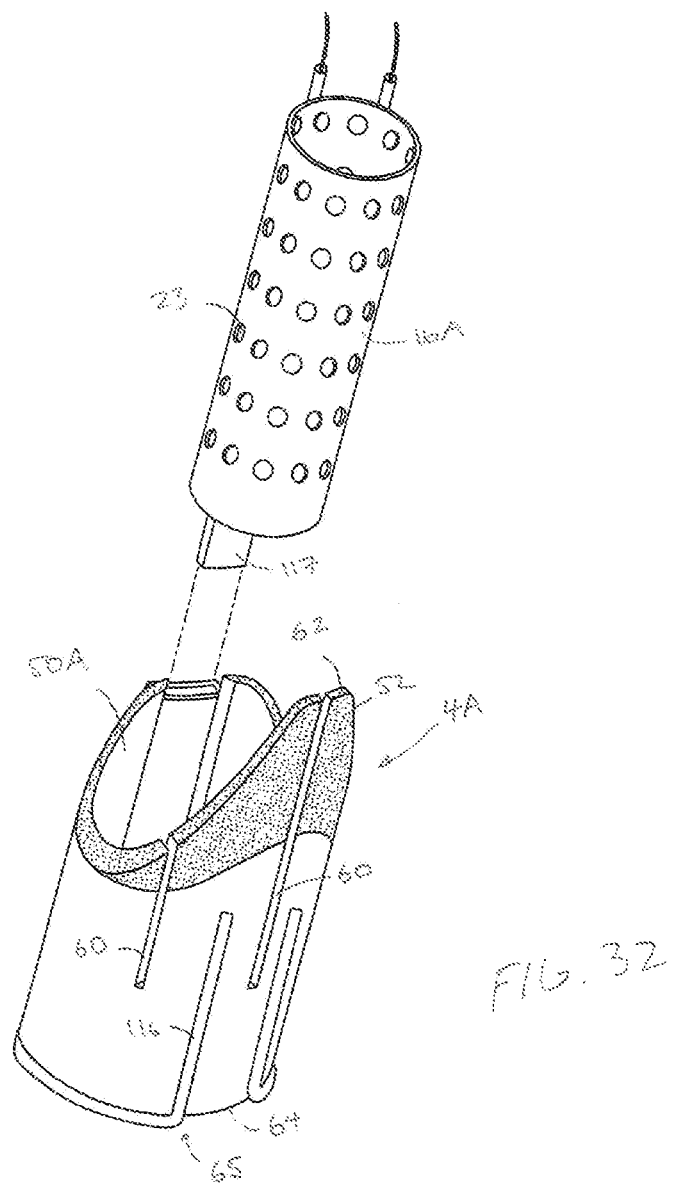

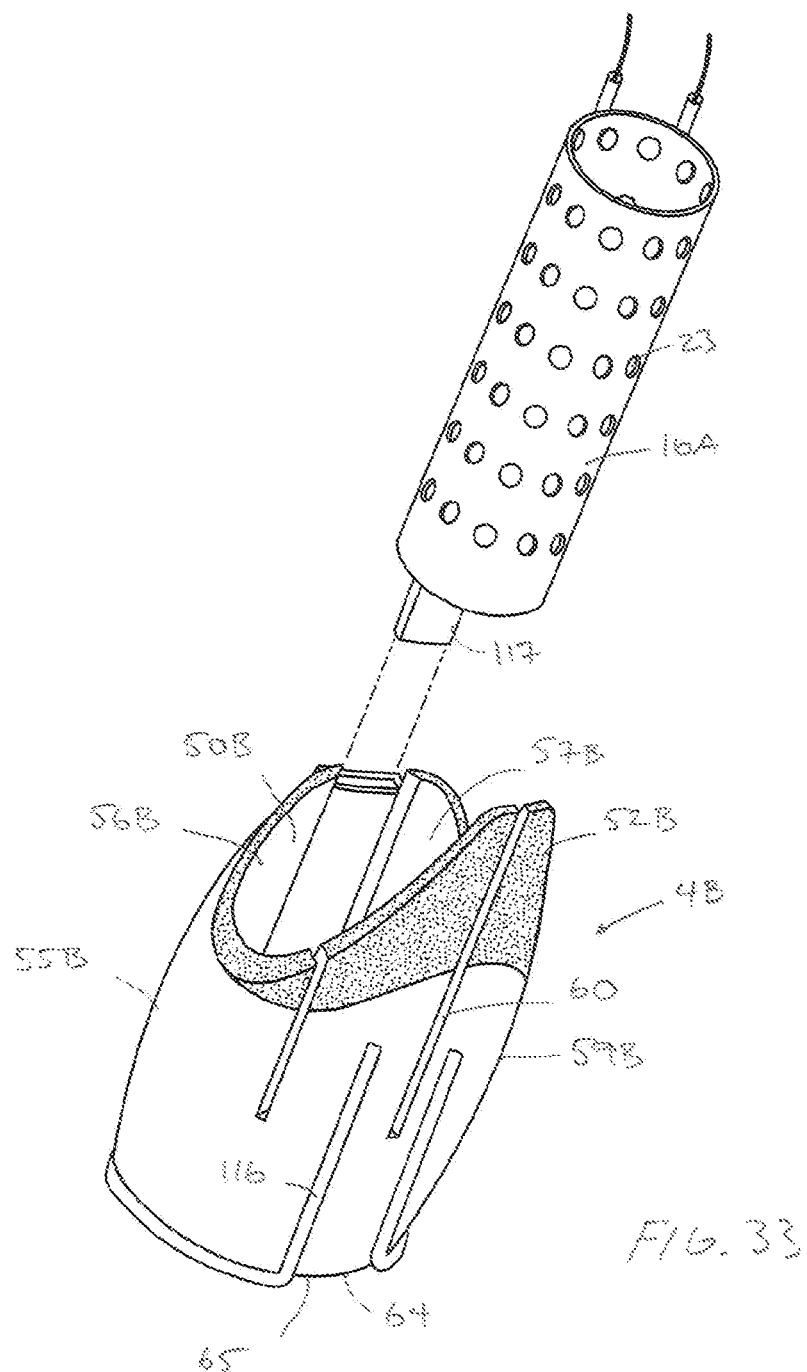

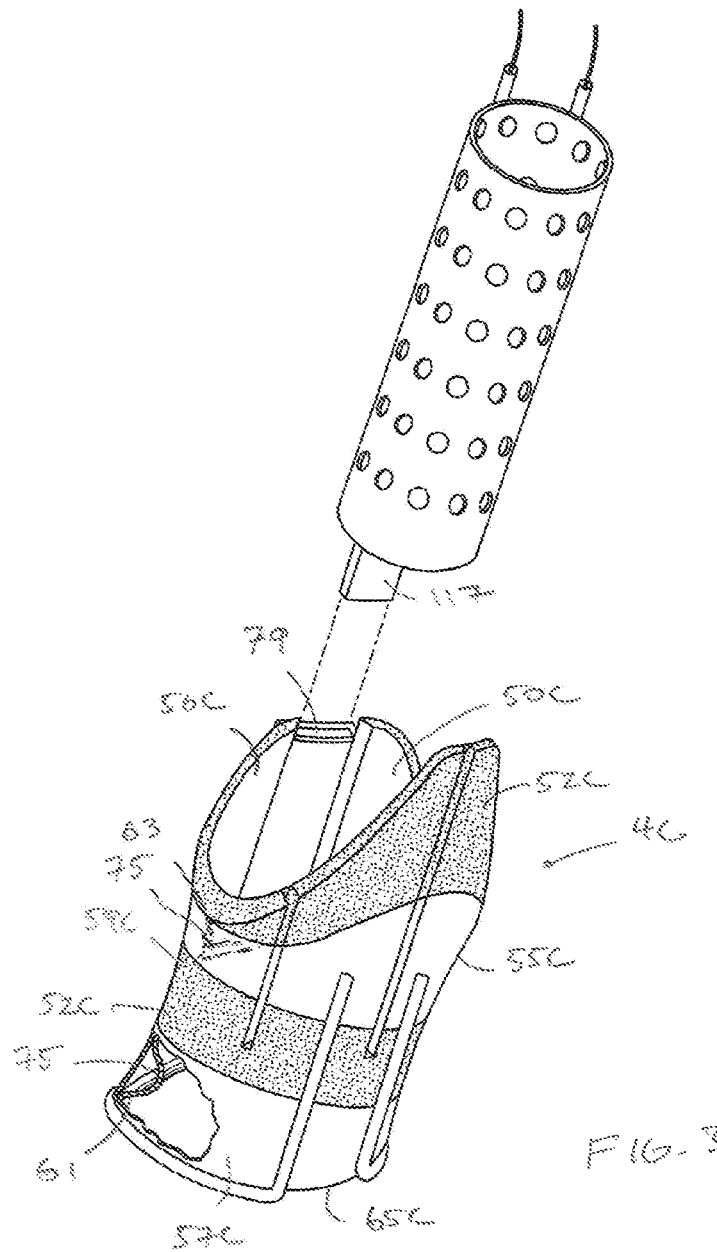

METHODS AND DEVICES FOR MANIPULATING AND FASTENING TISSUE

CROSS REFERENCE TO RELATED APPLICATIONS

The present application is a division of U.S. application Ser. No. 15/861,785 filed Jan. 4, 2018, which is a division of U.S. application Ser. No. 14/558,865 filed Dec. 3, 2014, now U.S. Pat. No. 9,861,360 issued Jan. 9, 2018, which is a division of U.S. application Ser. No. 13/229,061 filed Sep. 9, 2011, now U.S. Pat. No. 8,915,929 issued Dec. 23, 2014, the entirety of each of which are incorporated herein by reference.

BACKGROUND OF THE INVENTION

The present invention relates to methods and devices for manipulating and fastening tissue. In particular, the present invention may be useful in treating gastroesophageal reflux disease (GERD).

Referring to FIG. 2, a normal stomach and esophagus are shown with a disease state shown in the dotted line position. GERD develops in the disease state since the gastroesophageal flap valve at the junction or intersection between the esophagus and stomach has deteriorated so that stomach contents can splash into the esophageal tract resulting in GERD. The disease state is associated with a shorter esophageal tract and a somewhat enlarged stomach. The junction has also moved orally thereby effectively shortening the esophageal tract as well.

SUMMARY OF THE INVENTION

The present invention provides devices and methods for manipulating and fastening tissue together. The device includes numerous aspects, which may be practiced by themselves or in combination with other aspects of the invention. The device will be described in connection with treating GERD but shall have applications in other fields as well.

The device includes a shaft and a tissue displacing element coupled to the shaft. The tissue displacing element is configured to reshape stomach tissue. The stomach tissue is then fastened together to form a fold. When treating GERD the fold is formed at the intersection of the esophageal tract and stomach.

In one aspect of the invention, a plurality of tissue displacing elements are coupled to the shaft. The displacing elements are preferably individually and independently movable. The device may also include a common retractor, which is configured to displace the tissue displacing elements simultaneously. When used to recreate the junction between the esophagus and stomach, the common retractor may be moved distally along the shaft to lengthen the fold of tissue. The device may include a lock, which couples two tissue displacing elements together while maintaining the ability to independently move, or maintain stationary, the third element. In this manner, two of the tissue displacing elements may be simultaneously moved while at least one tissue displacing element remains stationary.

The tissue displacing element may include an elongate element, such as a wire, having an engaging element, such as a helical coil, at the distal end. Once the coil is rotated into tissue, the tissue is displaced by applying tension to the wire. The wire may have a curved distal portion so that rotation of the wire changes a position and angular orientation of the wire. A sheath may be slidable over the wire to cover and uncover the distal portion of the wire. The shape of the distal portion changes when the sheath covers and uncovers the wire thereby providing greater flexibility in directing the coil to engage a particular stomach location.

In another aspect of the invention, the device may include a tissue shaper coupled to the shaft. Tissue may be moved into the tissue shaper by simply moving the tissue displacing element to draw tissue into the tissue shaper. Alternatively, tissue may be moved into the tissue shaper by moving only the tissue shaper or the tissue shaper and the tissue displacing element simultaneously. The shaper has a cavity with an open proximal end leading to the cavity. The tissue displacing element may be movable within the cavity and to positions proximal and distal to the cavity. The tissue shaper may also be removable from the shaft and replaceable with another shaper. The shaft may include a primary shaft and a secondary shaft, which are slidable relative to one another, the tissue shaper being coupled to the primary shaft and the tissue displacing element being coupled to the secondary shaft.

The tissue shaper may also be partially or completely resilient so that the cavity may be expanded and to provide compression on tissue as tissue enters the cavity. The elastomeric portion may be positioned at the proximal open end of the cavity so that the proximal end may expand to accommodate tissue. The cavity may also include an elastomeric portion adjacent a midportion of the cavity. The flexibility of the tissue shaper may also be enhanced by providing a plurality of longitudinal slits in the tissue shaper. The device may also include a tension sensor coupled to the tissue displacing element. The tension sensor measures tension on the tissue displacing element developed during displacement of tissue.

The shaft may include a vacuum orifice configured to adhere the shaft to tissue. The vacuum orifice may be used to grasp the esophageal tract. The vacuum orifice may be used to stabilize tissue displaced by the tissue displacing element so that the tissue displacing element may be released and repositioned to displace another part of the stomach while the vacuum orifice holds previously displaced stomach tissue.

The device may also include a tissue shifting element configured to shift tissue held by the shaper. The tissue shifting element may be configured to engage a stomach side of the fold and displace the stomach side of the fold distally thereby moving the intersection of the fold distally. Alternatively, the tissue shifting element may displace both tissue layers such as the esophageal side and the stomach side when treating GERD. The tissue shifting element displaces tissue to increase a length of the fold of tissue while the fold of tissue is positioned in the cavity. The tissue shifting element may also draw tissue into the shaper while shifting tissue already held by the shaper.

The device may include a fastener applier which is a separate device delivered down a fastener lumen in the shaft. The fastener applier may include a fastener cartridge containing a plurality of fasteners and may deliver a plurality of fasteners in a single actuation. The fastener cartridge may apply a compressive force to the fold of tissue prior to application of the fastener.

The common retractor may include a slot in which the tissue displacing element is positioned so that the central axis of the wire translates within the slot. Movement within the slot changes an angular position by at least 45 degrees with respect to the longitudinal axis of the shaft when moving within the slot. The change in angular position provided by the slot may be accomplished without moving the shaft.

These and other features and aspects of the invention will become apparent from the following description of the preferred embodiment, drawings and claims.

BRIEF DESCRIPTION OF DRAWINGS

FIG. 4 shows a perspective view of the device.

FIG. 5 is a cross-sectional view of the device at line A-A of FIG. 4.

FIG. 6 is a cross-sectional view of the device of FIG. 5 with guide tubes moved within slots to translate the tissue displacing elements.

FIG. 7 shows the range of motion provided by the tissue displacing element and the range of motion provided when the sheath is used.

FIG. 8 shows a tissue shifting element in a stored position.

FIG. 9 shows the tissue shifting element engaging one tissue layer of the tissue fold.

FIG. 10 shows the tissue shifting element engaging both tissue layers of the tissue fold.

FIG. 11 shows a fastener applier, which may be used with the present invention.

FIG. 13A shows another fastener applier prior to delivery of the fastener.

FIG. 13B shows the fastener of FIG. 13A delivered into the tissue fold.

FIG. 20 shows all three tissue displacing elements engaged with tissue and positioned proximate a common retractor.

FIG. 27 shows the tissue displacing element retracted to displace tissue toward the tissue shaper.

FIG. 28A shows the tissue displacing element moved within the slot to displace tissue toward an end of the tissue shaper.

FIG. 28B shows the tissue displacing element of FIG. 28A moved into the tissue shaper.

FIG. 31 shows tissue extending through an open distal end of the shaper for manipulation by the tissue displacing elements.

FIG. 32 shows the device with a removable tissue shaper attached to the shaft.

FIG. 33 shows the device with another tissue shaper attached to the shaft.

FIG. 34 shows the device with still another tissue shaper attached to the shaft.

DESCRIPTION OF THE PREFERRED EMBODIMENTS

Figure 1:
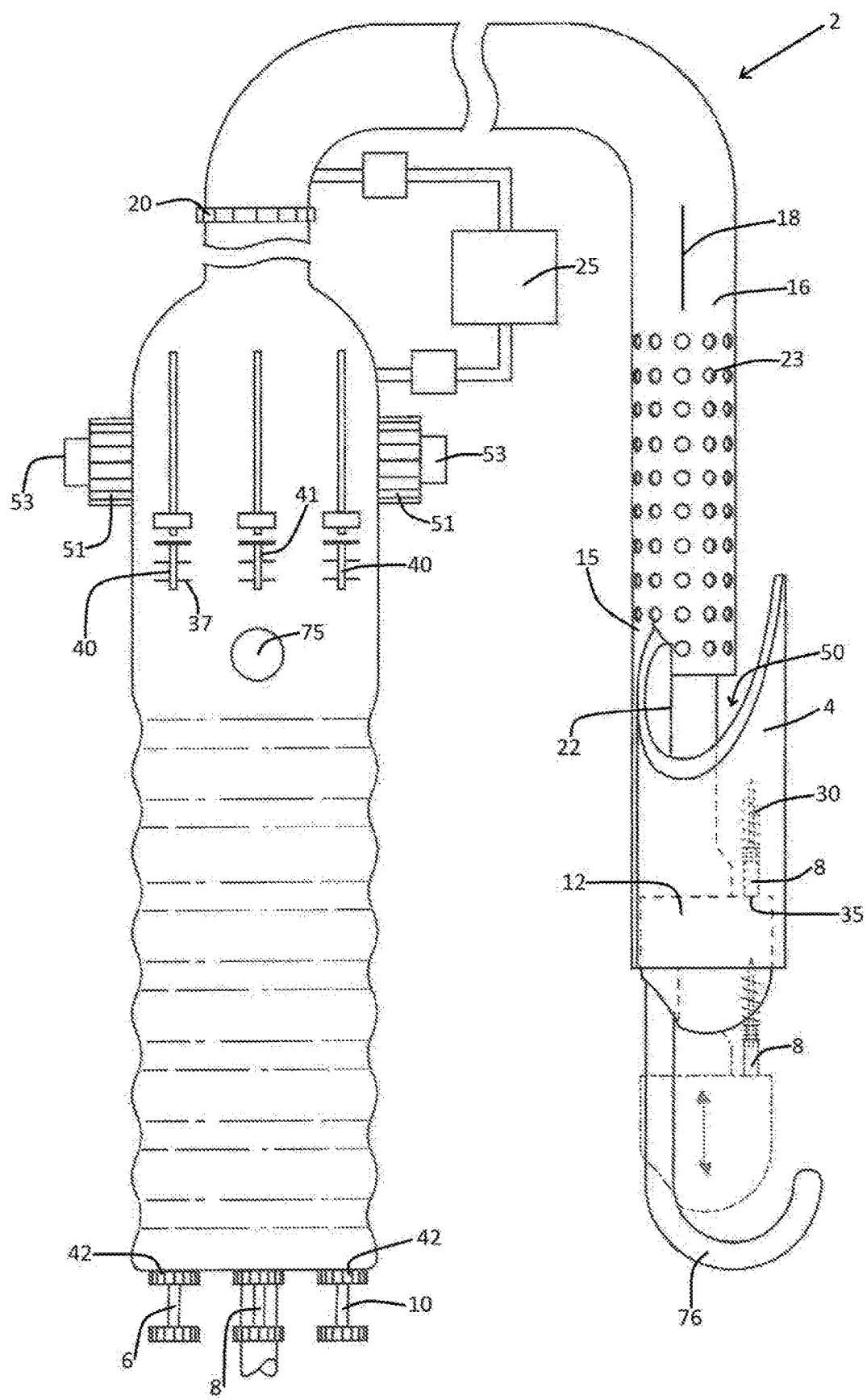
FIG. 1 shows a device for manipulating and fastening tissue of the present invention.
Figure 2:
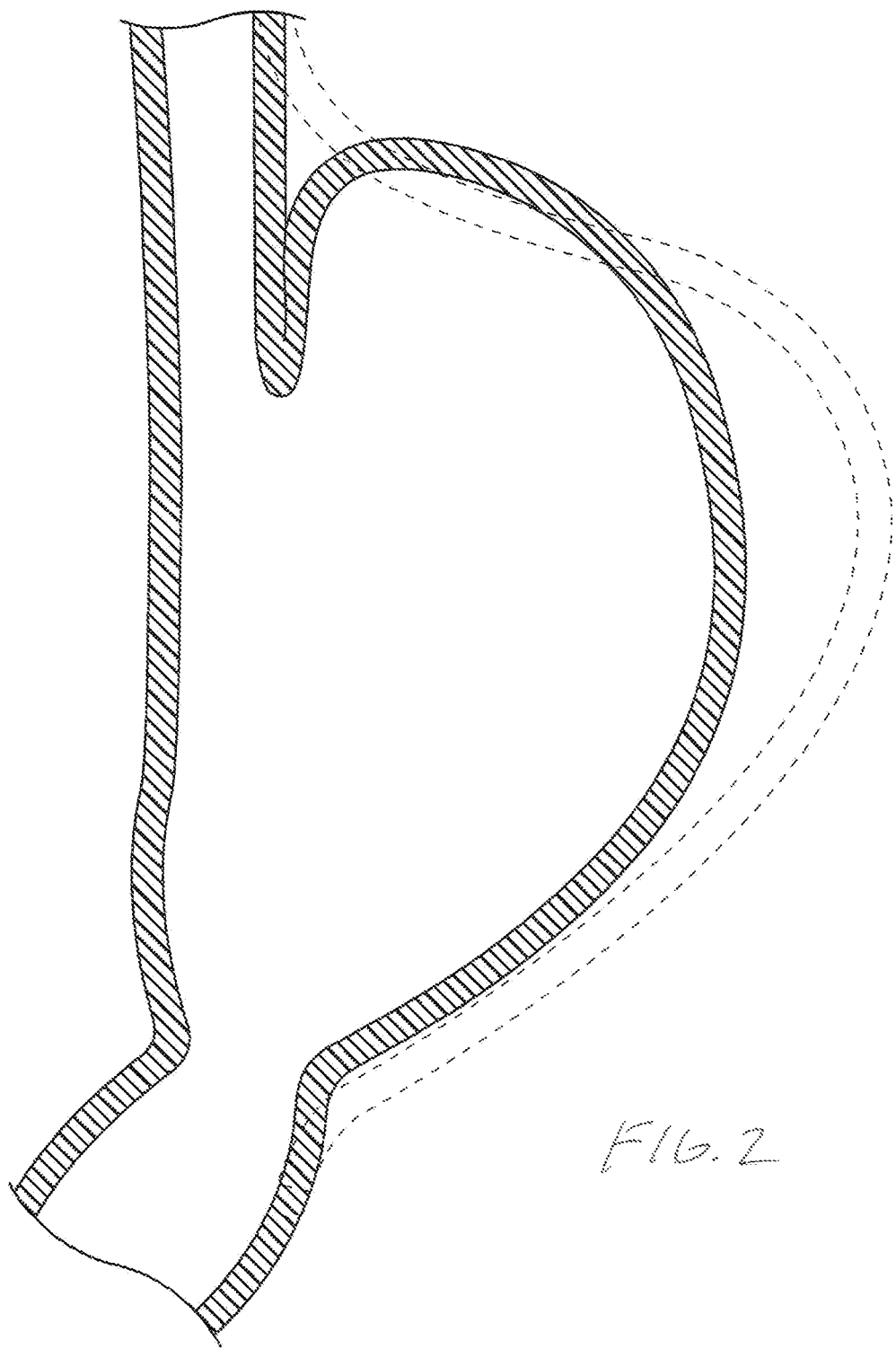
FIG. 2 shows a stomach and an outline of the stomach in a disease state.

Referring to FIGS. 1, 4 and 5, a device 2 for manipulating and fastening tissue is shown. The device 2 and various aspects thereof may be used to manipulate and fasten tissue anywhere in the body. In particular, the device 2 of the present invention may be used to manipulate stomach tissue to recreate the intersection between the stomach and the esophageal tract.

The device 2 includes a tissue shaper 4 which shapes tissue into a desired shape such as a gastroesophageal flap valve. The device 2 has first, second and third tissue displacing elements 6, 8, 10 which gather and manipulate tissue into a cavity 50 in the tissue shaper 4. The tissue displacing elements 6, 8, 10 are coupled to a common retractor 12 having a platform 14 which may be used to simultaneously move the tissue displacing elements 6, 8, 10 as described below. The tissue shaper 4 is coupled to a shaft 15 consisting of a flexible primary shaft 16 and a flexible secondary shaft 22 and may be releasably coupled to the shaft 15 as described below. The shaft 15 defines a longitudinal axis 18 and angular orientations and displacements are often defined and described herein as being relative to the longitudinal axis 18. For example, referring to FIG. 6, an angle B is defined between the first and second tissue displacing elements 6, 8 as defined relative to the longitudinal axis 18. The longitudinal axis 18 may be substantially straight or may be curved without departing from the scope of the invention so long as the longitudinal axis 18 generally follows and defines the orientation of the shaft 15. The primary shaft 16 terminates at the proximal end at a lock 20 which locks and seals the primary shaft 16 to the secondary shaft 22. When the lock 20 is unlocked, the primary and secondary shafts 16, 22 may be moved relative to one another. The primary and secondary shafts 16, 22 are movable relative to one another so that the common retractor 12 and platform 14 are movable as shown by the solid and dotted line positions of FIG. 1 although the common retractor 12 has greater range of motion than depicted in both directions. A plurality of vacuum orifices 23 are positioned on the primary shaft 16 to grasp tissue, such as the esophageal tract, as also described below. The vacuum orifices 23 are coupled to a suction source 25 through a space between the first and second shafts 16, 22.

The tissue shaper 4 forms a fold of tissue which is substantially similar to a natural gastroesophageal flap valve. To this end, the tissue shaper 4 forms a generally tubular structure open on both ends, the esophagus on one side and the stomach on the other. The generally tubular structure may also have an open side proximate the esophagus or may be a substantially closed shape. Referring to FIGS. 5 and 6, the tissue shaper 4 has a generally curved cross-sectional shape terminating at a first end 24 and a second end 26. The curved cross-sectional shape forms an arc of at least 180 degrees relative to the longitudinal axis between the first and second ends 24, 26. The tissue shaper 4 also defines a central plane 28 (FIG. 6) which lies equidistant from the first and second ends 24, 26 and/or may define an axis of symmetry when viewed along the longitudinal axis 18. The second tissue displacing element 8 lies on the central plane 28 but may be offset from the plane 28 as well.

The tissue shaper 4 may, of course, take other suitable cross-sectional shapes such as oval, round, or V-shaped without departing from the scope of the invention and it is understood that these shapes also would have a central plane as defined herein. Furthermore, the tissue shaper 4 may also be omitted without departing from various aspects of the present invention. For example, the tissue displacing elements 6, 8, 10 alone may be used to displace stomach tissue and form a fold of tissue by simply displacing the tissue in a manner which forms the fold of tissue without requiring the tissue shaper 4. The tissue may be displaced into the shaper 4 without moving the shaper 4 and using only elements 6, 8 10, moving only the tissue shaper 4, or moving both the elements 6, 8, 10 and shaper together.

Referring to FIG. 7, the tissue displacing elements 6, 8, 10 each include a tissue engaging element 30, such as a helical coil 32, which is rotated to pierce and engage tissue as is known in the art. The coil 32 is coupled to an elongate element 34, such as a wire 35, and the elongate element 34 is covered by a retractable sheath 36. The elongate element 34 may have a curved shape which permits the user to direct the distal end in a desired direction by simply rotating element 30. The sheath 36 may be advanced over the wire 35 to change the shape of the distal portion to provide a broader range of motion to direct the coil 32 as desired. FIG. 7 shows the elongate element 34 bent further by the sheath 36, however, the sheath 36 could also straighten the elongate element 34. Furthermore, the elongate element 34 or sheath 36 may be substantially straight, rather than bent, without departing from the scope of the invention.

As will be described further below, the tissue engaging elements 6, 8, 10 may be used to displace tissue substantially longitudinally when the wire 35 is retracted. The elements 6, 8, 10 may be retracted into and extended from the shaft as shown throughout the Figures. The curved shape of the wire 35 may also provide an angular displacement (change in orientation) with respect to the longitudinal axis 18 of at least 45 degrees when the element 6, 8, 10 is retracted. Stated another way, the elements 6, 8, 10 may apply an angular displacement of at least 45 degrees relative to the ends 24, 26 of the tissue shaper 4 (in addition to longitudinal displacement) when the wire 35 is retracted. This aspect of the invention will be described in greater detail below. The angular displacements or change in angular orientation is accompanied by longitudinal displacement toward the patient's feet and into the stomach of at least 5 cm and is typically 2 to 6 cm.

Figure 3:
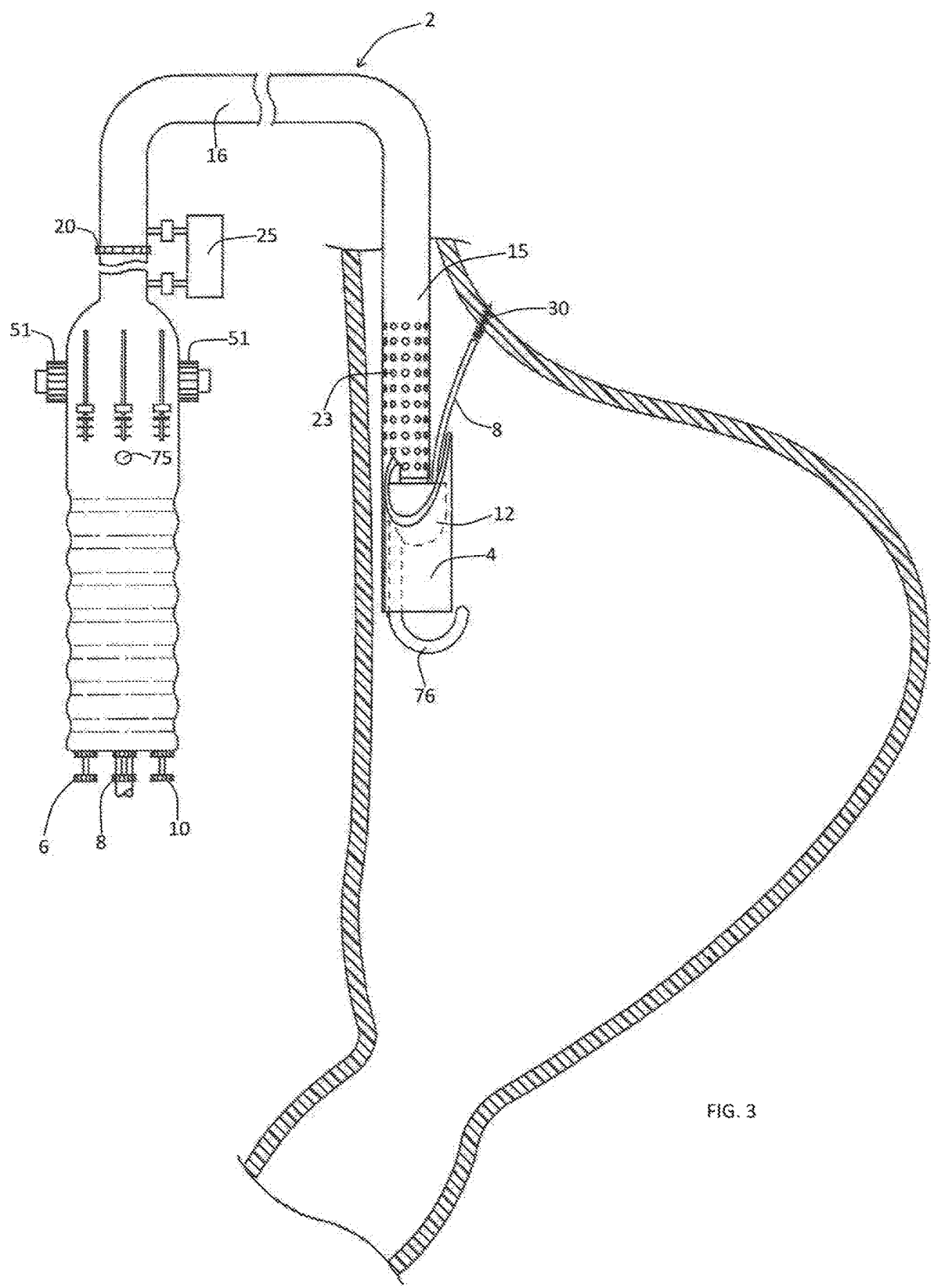
FIG. 3 shows the device inserted into the stomach and a tissue engaging element extended to engage stomach tissue.

Once the helical coil 32 has engaged tissue as shown in FIG. 3, tension is applied to the elongate element 34 to move the stomach tissue toward the tissue shaper 4. The elongate element 34 may be coupled to a tension sensing element, such as a simple spring element 41 shown in dotted line with only element 8, which displays an indication of tension on the elongate element at an indicator 40. Use of the tension indicators 40 is described below in connection with use of the device 2. The tissue engaging element 6, 8, 10 may grip tissue using any other suitable method including graspers or a suction gripper without departing from the scope of the invention. A twist lock 42 is provided to lock each of the tissue displacing elements 6, 8, 10 at any suitable position relative to the secondary shaft 22 and maintain tension on the elongate elements 34.

Figure 16:
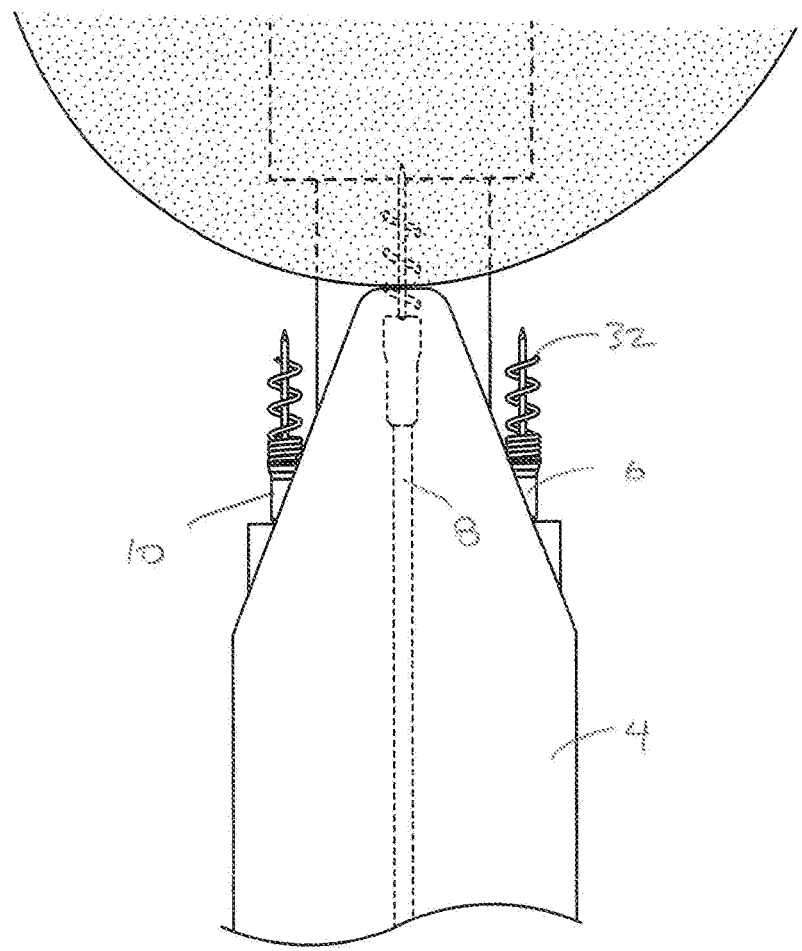
FIG. 16 shows a second tissue displacing element engaging stomach tissue.
Figure 17:
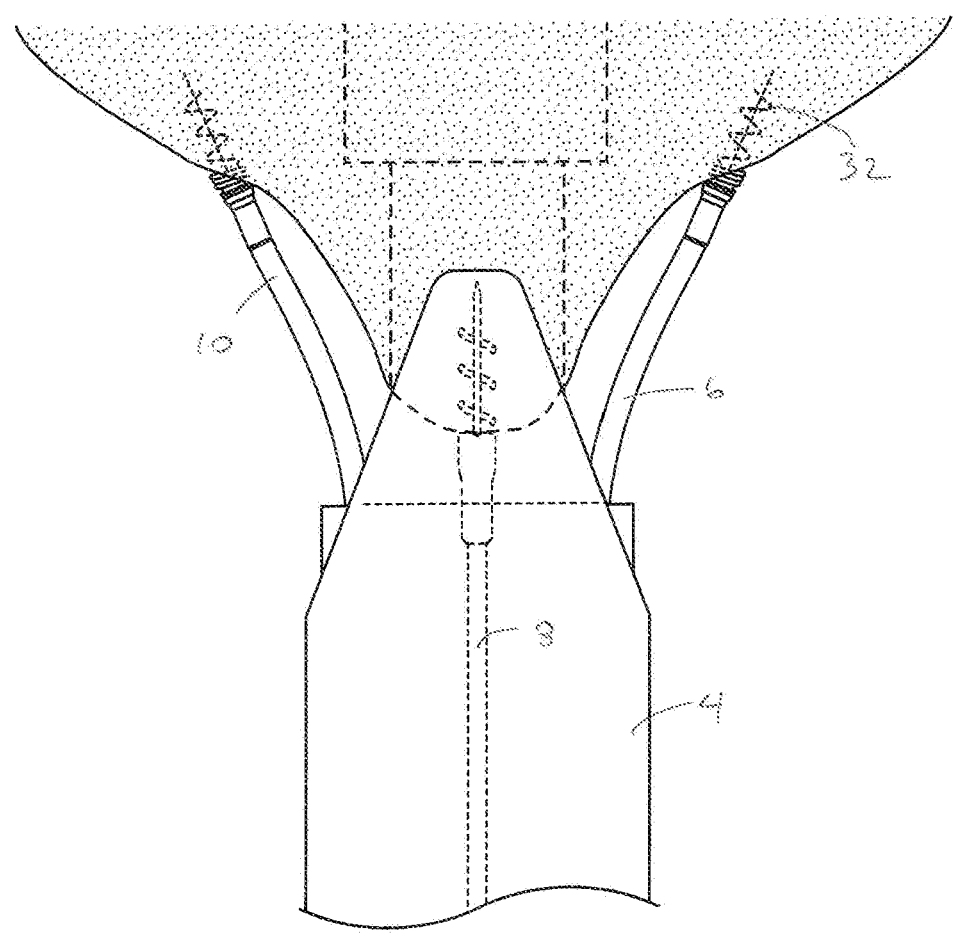
FIG. 17 shows the first and third tissue displacing elements engaging stomach tissue after retracting stomach tissue with the second tissue displacing element.
Figure 18:
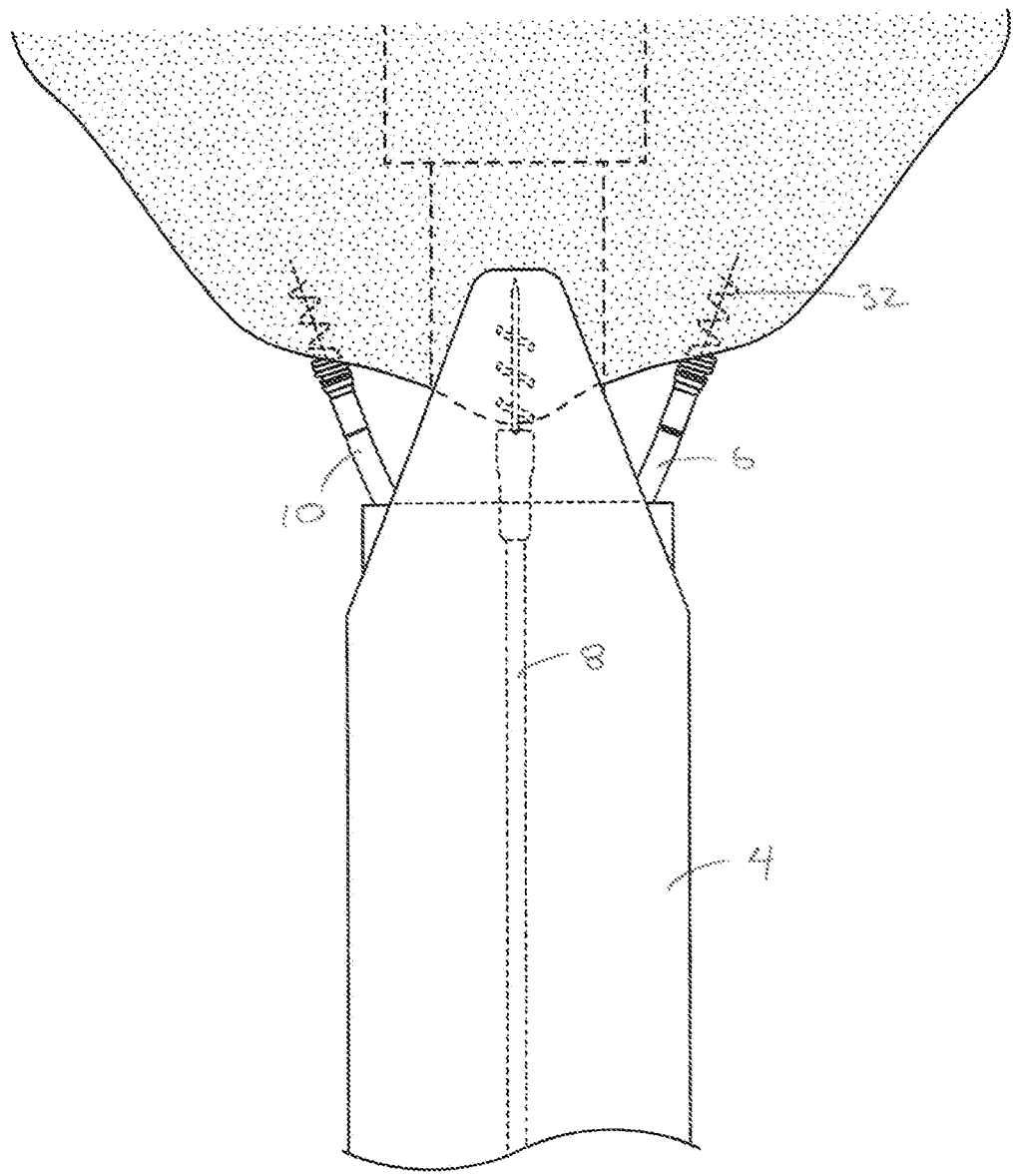
FIG. 18 shows the first and third tissue displacing elements retracting stomach tissue after engagement with tissue in FIG. 17.
Figure 19:
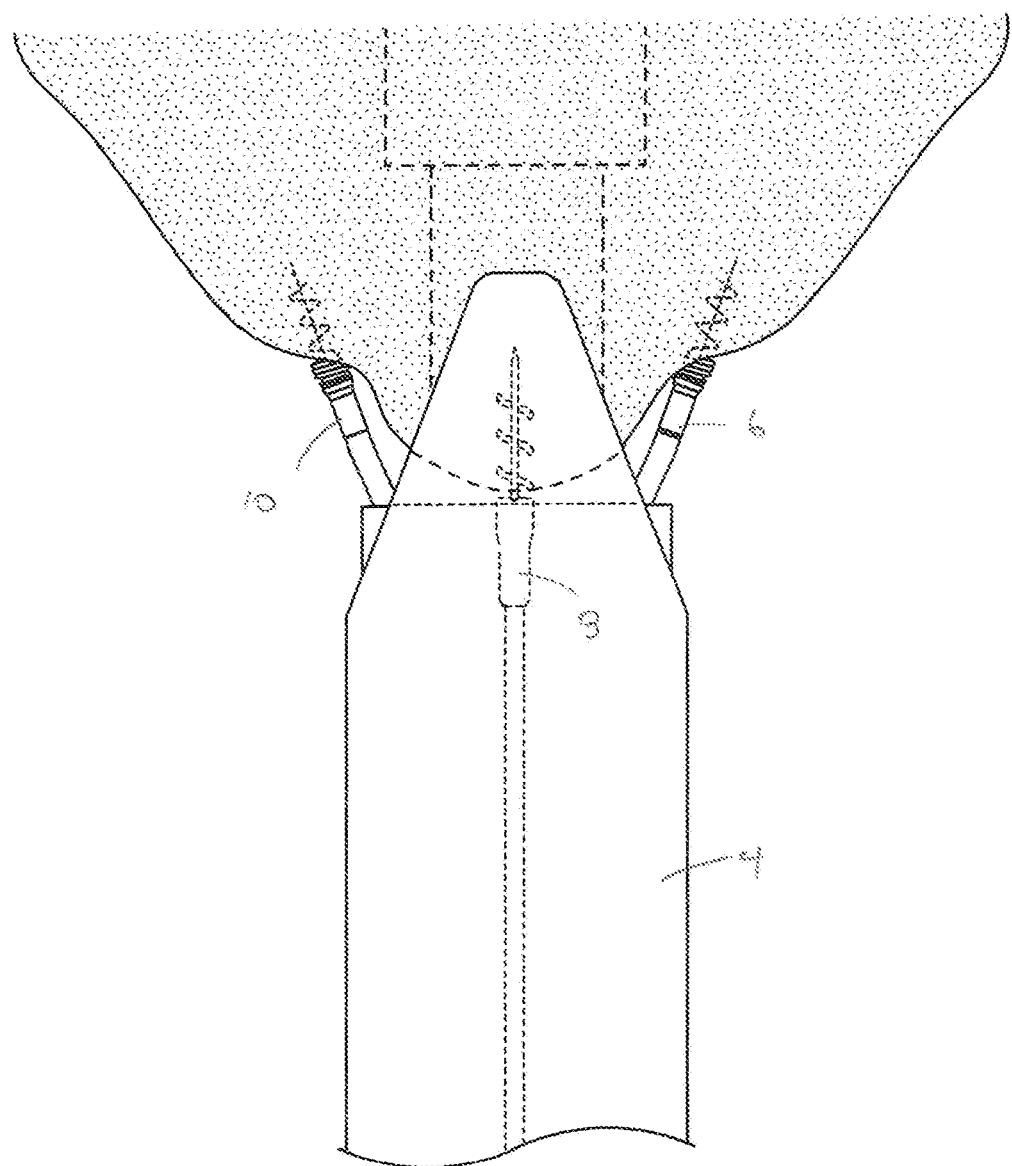
FIG. 19 shows the second tissue displacing element disengaged from stomach tissue, reengaged with stomach tissue and retracted again while the first and third tissue displacing elements maintain the tissue fold.
Figure 2D:
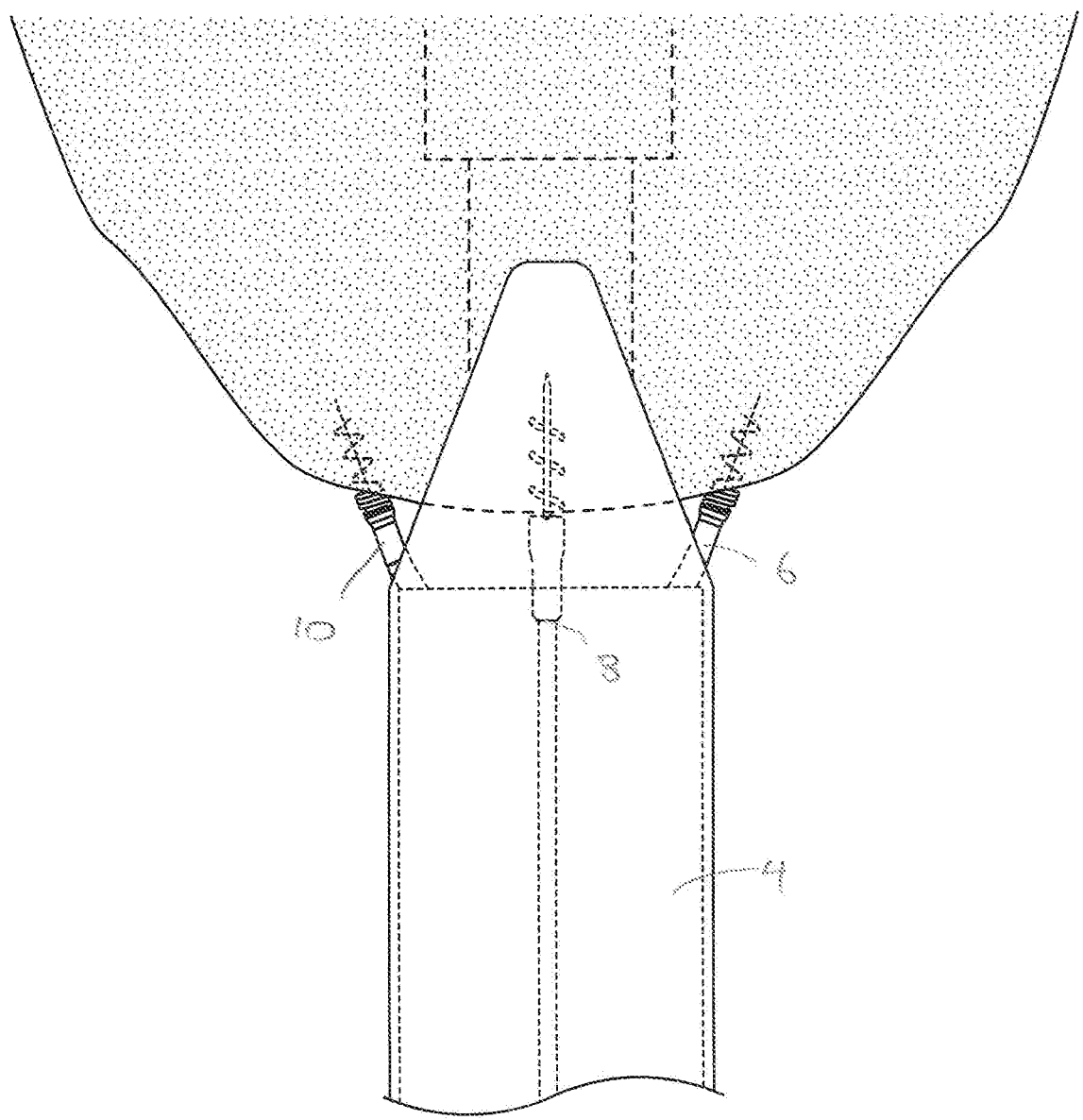

Referring to FIG. 16, in one aspect of the present invention, one of the tissue displacing elements 6, 8, 10, such as the second tissue displacing element 8, may be displaced until a threshold tension is reached at which time the user applies the appropriate lock 42 (see FIG. 1) to lock the tissue displacing element 8 as shown in FIG. 17. As also shown in FIG. 17, the user may manipulate another of the elements 6, 10 until another threshold tension or displacement is reached at which time the user again applies the appropriate lock 42 as shown in FIG. 18. The second tissue displacing element 8 may then be disengaged, moved, reengaged with tissue and retracted again as shown in FIG. 19. In this manner, the user may continue to individually displace each of the tissue displacing elements 6, 8, 10, while maintaining engagement with the other elements until the desired shape is achieved. The tension indicators 40 may be used with any method described herein even when not expressly described.

The first and third tissue displacing elements 6, 10 are also movable within elongate slots 44 in the platform between the position of FIG. 5 near the ends 24, 26 of the shaper 4 to the position of FIG. 6 closer to the second element 8. The sheath 36 and elongate element 34 are positioned in guide tubes 46 which are movable in the slots 44 by manipulating pull wires 48. The pull wires 48 are coupled to an actuator, such as a control knob 51, which is simply rotated to move both pull wires 48 thereby moving the guide tube 46 within the slot 44. A locking button 53 is provided to lock each of the control knobs 51 to fix the position of the pull wires 48 and therefore fix the position of the guide tube 46 anywhere along the slot 44.

The slot 44 permits the tissue displacing element 6, 10 to be moved so that a central axis 56 of the elongate element 34 is displaced at least 45 degrees relative to the longitudinal axis 18 when viewed along the longitudinal axis 18 as shown in FIG. 6 and represented by angle C. Stated another way, a portion 35 (FIG. 1) of the elongate element 34 positioned at the slot 44 which emerges from shaft 15 changes angular position by at least 45 degrees with respect to the longitudinal axis 18. Movement in this manner is typically not possible with conventional multi-link arms and graspers which have a base which may pivot but is fixed in translation relative to the shaft.

The slots 44 may also lie generally on a plane defined by the platform 14 which is substantially perpendicular to the longitudinal axis 18 of the primary shaft 16. Stated still another way, the slots 44 permit the tissue displacing elements 6, 8, 10 to change an angle B formed between each of the first and third tissue displacing elements 6, 10 and the second tissue displacing element 8, or the central plane 28, by at least 45 degrees relative to the longitudinal axis 18. In this manner, the slots 44 may be used to displace tissue toward and away from the ends 24, 26 of the tissue shaper 4. The elongate element 34 may be retracted into the guide tube 46 so that the helical coil 30 is positioned at the slot 44 (see FIGS. 27 and 28). When the coil 30 is positioned at the slot 44, translation of the coil 30 in the slot 44 shifts tissue without longitudinal displacement which is useful in various methods described below.

The tissue shaper 4 of FIG. 4 is configured to shape a fold of tissue to recreate a gastroesophageal flap valve. The tissue shaper 4 has a cavity 50 which receives the tissue. As mentioned above, the tissue can be moved into the cavity 50 by moving the elements 6, 8, 10 or shaper 4 alone or by moving the shaper 4 and elements 6, 8, 10 together.

Referring to FIG. 4, the tissue shaper 4 may include an elastomeric portion 52 on a proximal portion 54 of the tissue shaper 4 which permits the cavity 50 to expand to accommodate tissue. The elastomeric material 52 is positioned at a proximal opening 56 of the cavity 50 so that the opening 56 can elastically expand thereby facilitating introduction of a larger tissue volume while applying a modest compressive force to tissue at the opening 56. The tissue shaper 4 will also increase compression on tissue contained in the cavity 50 as the tissue volume increases. The tissue shaper 4 has an outer wall 58 which may have a plurality of slits 60 formed therein to further increase the flexibility of the tissue shaper 4 and permit expansion of the cavity 50. The slits 60 extend from the proximal end 62 and extend toward a distal end 64 of the tissue shaper 4. The distal end 64 of the tissue shaper 4 also has a distal opening 65 to permit the tissue to extend through the tissue shaper 4 as described below in connection with use of the device 2. The tissue shaper 4 may be a substantially fixed structure except for the elastomeric portion 52, however, the elastomeric portion 52 does provide some movability to the tissue shaper 4 in that the cavity 50 has a first volume during introduction which is less than a volume of the cavity 50 when tissue is introduced into the expandable cavity 50. As such, the tissue shaper 4 does change shape even though the tissue shaper 4 is not movable by the user. Although the tissue shaper 4 is shown as a structure, which is not moved by the user, the tissue shaper 4 may be movable by the user to close the tissue shaper 4 (not shown) around the fold of tissue without departing from numerous aspects of the present invention.

Referring now to FIG. 32, a removable tissue shaper 4A is attached to a primary shaft 16A. The tissue shaper 4A may be removably attached to the shaft 15 in any suitable manner such as a simple snap-fit connection 117 or bayonette connection (not shown). Referring to FIGS. 33 and 34, two more tissue shapers 4B, 4C are shown with the tissue shapers 4A, 4B, 4C being interchangeable and usable in any manner that tissue shaper 4 is used. The user may decide upon which tissue shaper 4A, 4B, 4C to use prior to beginning the procedure and attach the appropriate tissue shaper 4A, 4B, 4C to the shaft 16A. Alternatively, the user may begin the procedure with one of the tissue shapers 4A, 4B, 4C and may decide to change to another shaper (different shape and/or size). The present invention provides the ability to change shapers 4A, 4B, 4C or select the appropriate shaper 4A, 4B, 4C from available shapes and sizes.

The tissue shaper 4, 4A may have substantially straight edges, forming an acute angle, symmetrically disposed about the longitudinal axis 18 (see FIG. 1 and FIG. 16). Alternatively, the profile edges could be convex or concave, or any combination of concave, convex or straight edged profiles as now discussed in connection with tissue shapers 4B, 4C of FIGS. 33 and 34. Referring to FIG. 33, for example, tissue shaper 4B has a convex outer wall 55B which creates a cavity 50B also having a convex outer wall 57B. A proximal opening 56B leading to the cavity 50B has a smaller cross-sectional shape than a midportion 59B of the cavity 50B. In this manner, the cavity 50B may be sized to hold the fold of tissue more loosely in the midportion 59B so that the tissue in the midportion 59B may be manipulated more easily within the cavity 50B while the tissue fold is still being firmly held by the proximal opening 56B. Use of elastomeric portion 52B may be particularly advantageous in holding tissue firmly at the proximal opening 56B.

Referring to FIG. 34, tissue shaper 4C has a concave outer wall 55C and a cavity 50C having a concave outer wall 57C. The cavity 50C has a proximal opening 56C, a distal opening 65C and a midportion 59C. The midportion 59C has the smallest cross-sectional shape throughout the cavity 50C so that tissue contained in the cavity 50C may be held more firmly by the midportion 59C. An elastomeric portion 52C of the shaper 4C may be adjacent the midportion 59C which provides the advantages described above in connection with tissue shaper 4. Holding tissue within the shaper 4C in this manner may facilitate gathering tissue using various methods described herein. For example, the tissue shaper 4C may hold the fold of tissue firmly at the midportion 59C so that tissue near the distal opening 65C and extending through the distal opening 65C may be manipulated.

The tissue shaper 4C also includes a first clamping element 61 and a second clamping element 63 (shown in dotted-line position). The first and second clamping elements 61, 63 may be elastic balloons 75 but may be any other suitable mechanism such as a pivoting jaw. FIG. 34 shows the balloons 75 partially inflated to clamp tissue contained in the tissue shaper 4C. The first clamping element 61 is positioned near the distal end and the second clamping element 63 is positioned along the midsection although any number of clamping elements (including only one) may be used. An inflation lumen 79 is coupled to the balloons 75 and extends through the connector 117 but may be a separate lumen as well. It is understood that the clamping elements 61, 63 may be incorporated into any of the other tissue shapers 4, 4A, 4B and use of the clamping elements 61, 63 with the any of the other tissue shapers 4, 4A, 4B is expressly incorporated here.

The clamping element 61, 63 may be used to hold tissue contained within the tissue shaper 4C and may be clamped and unclamped as desired. As such, the balloons 75 may be deflated during the tissue displacing steps and inflated to hold tissue after the displacing step. Thus, all methods described herein may include deflating the balloon 75 prior to displacing tissue and/or may include inflating the balloon 75 after each displacing step. The clamping elements 61, 63 may also be used to hold tissue during application of fasteners and, to this end, each method described herein may include the step of clamping the tissue fold together before fastening the fold together. The clamping element 61, 63 may be released and again reapplied before each fastening step as desired and, again, all methods described herein shall expressly provide for the clamping steps described herein.

As mentioned above, the common retractor 12 and platform 14 are coupled to the secondary shaft 22 so that the platform 14 may be moved relative to the shaper 4. Movement of the secondary shaft 22 and the platform 14 also moves all three of the tissue displacing elements 6, 8, 10 simultaneously. The secondary shaft 22 includes lumens 66 which receive the tissue displacing elements 6, 8, 10 and pull wire lumens 68 which receive the pull wires 44 for the guide tubes 46 (FIGS. 5 and 6). A suction lumen 70 may also be provided which is coupled to vacuum orifices 72 in the platform 14. The vacuum orifices 72 and vacuum orifices 23 in the primary shaft 16 are coupled to a suction source 71 as shown in FIG. 1 and are independently controllable as is known in the art.

A visualization lumen 74 is formed between the primary and secondary shafts 16, 22 in which a visualization device 76 may be positioned. The visualization device 76 may be any suitable device and suitable devices are described in U.S. Pat. No. 7,583,872, Compact Scanning Fiber Device and U.S. Pat. No. 6,275,255, Reduced Area Imaging Devices. In one aspect of the present invention, the lumen 74 which receives the visualization device 76 is no more than 10% of a total cross-sectional area of the shaft 15. In one embodiment, the visualization lumen 74 may have a diameter of about 5 mm and the primary shaft 16 has a cross-sectional area of about 255 mm2. A lock 75 is also provided to couple movement of the first and third tissue displacing elements 6, 10 together as described below in connection with various methods of the present invention.

The tissue, or parts, thereof, may be stabilized or engaged within the tissue shaper 4, or even outside the tissue shaper 4, using the tissue displacing elements 6, 8, 10, the vacuum orifices 72 in the platform 14 or the vacuum orifices 23 on the primary shaft 16. Furthermore, it is understood that stabilizing tissue between tissue manipulations or fastening steps with any one of these elements may be practiced with any of the methods described herein even if not specifically described. For example, some methods of the present invention describe stabilizing tissue with the second tissue displacing element 8 while moving tissue with the first and/or third tissue displacing elements 6, 10 and such methods may be practiced by stabilizing tissue with any other suitable element such as the vacuum orifices 23 on the primary shaft 16 or vacuum orifices 72 in the platform 14 and such methods are expressly included as part of the invention.

The tissue shaper 4 may be sized to firmly hold the fold of tissue once the fold of tissue has been drawn into the cavity 50 while still permitting some movement of the tissue within the tissue shaper 4. Shifting tissue within the tissue shaper 4, as used herein, shall mean that the tissue shaper 4 holds the fold of tissue so that at least part of the tissue is approximated and in contact with one another prior to fastening but are still held loosely enough to shift tissue within the tissue shaper 4 and/or draw tissue into the tissue shaper 4.

Referring to FIGS. 8-10, one structure which may be used to move or shift tissue within the tissue shaper 4 is a tissue shifting element 110. The tissue shifting element 110 is coupled to the tissue shaper 4 and provides a mechanism for shifting tissue within the tissue shaper 4 without moving the tissue shaper 4 and preferably without moving the primary or secondary shafts 16, 22. The tissue shifting element 110 includes a pair of needles 112 mounted on a wire 114. The needles 112 may be coupled to the wire in any suitable manner; for example, the needles may pivotally engage the wire 114 or may have an integrally formed hinge with the wire 11. The device 2 may include two sets of needles 112. One set of needles 112A may pierce one tissue layer (FIG. 9) and the other set of needles 112 may penetrate both layers of the tissue fold (FIG. 10). Each wire 114 extends through a tube 116 having an open slit 118 through which the needles 112, 112A extend. When the wire 114 is advanced to the position of FIG. 8, the needles 112 are collapsed within the tube 116. When the wire 114 is moved proximally, the needles 112 naturally expand outwardly through the slit 118 and further proximal motion causes the needles 112, 112A to penetrate one or both tissue layers. The tissue shifting element 110 may engage the tissue with any other suitable mechanism including a movable suction port. Tissue may also be shifted within the tissue shaper 4 using elements 6, 8, 10 which may apply longitudinal and/or angular displacements as described herein. For example, the elements 6, 8, 10 may displace tissue further into the cavity 50 and displace tissue towards or away from the ends 24, 26 of the shaper 4 by moving the elements 6, 10 within slots 44. As such, the displacing elements 6, 8, 10 may also constitute tissue shifting elements for shifting tissue within the tissue shaper 4 as used herein. The tissue shifting element 110 is omitted for clarity in various drawings but all drawings including the tissue shaper 4 shall be interpreted to include the tissue shifting element 110.

Any suitable fastener may be used with the present invention and, in fact, numerous aspects of the present invention may be practiced with any other suitable fastening method such as adhesive or suture. Several suitable fastener appliers are described below in connection with FIGS. 11-14. Although the fastener applier is a separate device delivered down the fastener lumen 74, numerous aspects of the present invention may be practiced with the fastener applier being integrated into the device 2 rather than being a separate device. An advantage of providing a separate fastener applier is that the device 2 may be advanced down the patient's esophagus without the fastener applier positioned in the fastener lumen 74 which may provide a more flexible device for introduction than would a device having the fastener applier integrated into the device 2. The fastener lumen 78 includes a window 80 in the primary shaft 16 so that the fastener may be applied anywhere along an arc of at least 90 degrees, and may be at least 120 degrees, relative to the longitudinal axis 18 without moving the shaft 15 or the tissue shaper 4. The fastener lumen 74 may also include a ramp 80 which causes the fastener applier to be displaced radially outward from the longitudinal axis 18 to compress the fold of tissue prior to delivery of the fastener as described below and shown in FIG. 12.

Referring now to FIG. 11, a fastener applier 90 is shown. The fastener applier 90 includes a cartridge 92 containing a plurality of fasteners such as staples 94. An actuator 96 is coupled to a firing mechanism which is actuated to deploy the fasteners in any suitable fashion as is known in the art. The fastener applier 90 may be configured to deliver a plurality of staples 94 simultaneously and, in particular, in a longitudinal orientation. Different cartridges 92A, 92B may be provided to dispense a different number or orientation of staples 94 as desired and methods of the present invention may provide for sequential use of the cartridges 92, 92A, 92B. The fastener applier 90 may also be longitudinally movable with respect to the tissue shaper 4 and the primary shaft 16 so that the fastener applier 90 may be used at different longitudinal positions without moving the primary shaft 16 and/or the tissue shaper 4. Numerous aspects of the present invention may be carried out with the tissue fold being fastened in any suitable manner including use of an adhesive or conventional suture rather than discrete fasteners. Additional aspects of the fastener applier 90 are described in connection with use of the device.

Figure 12:
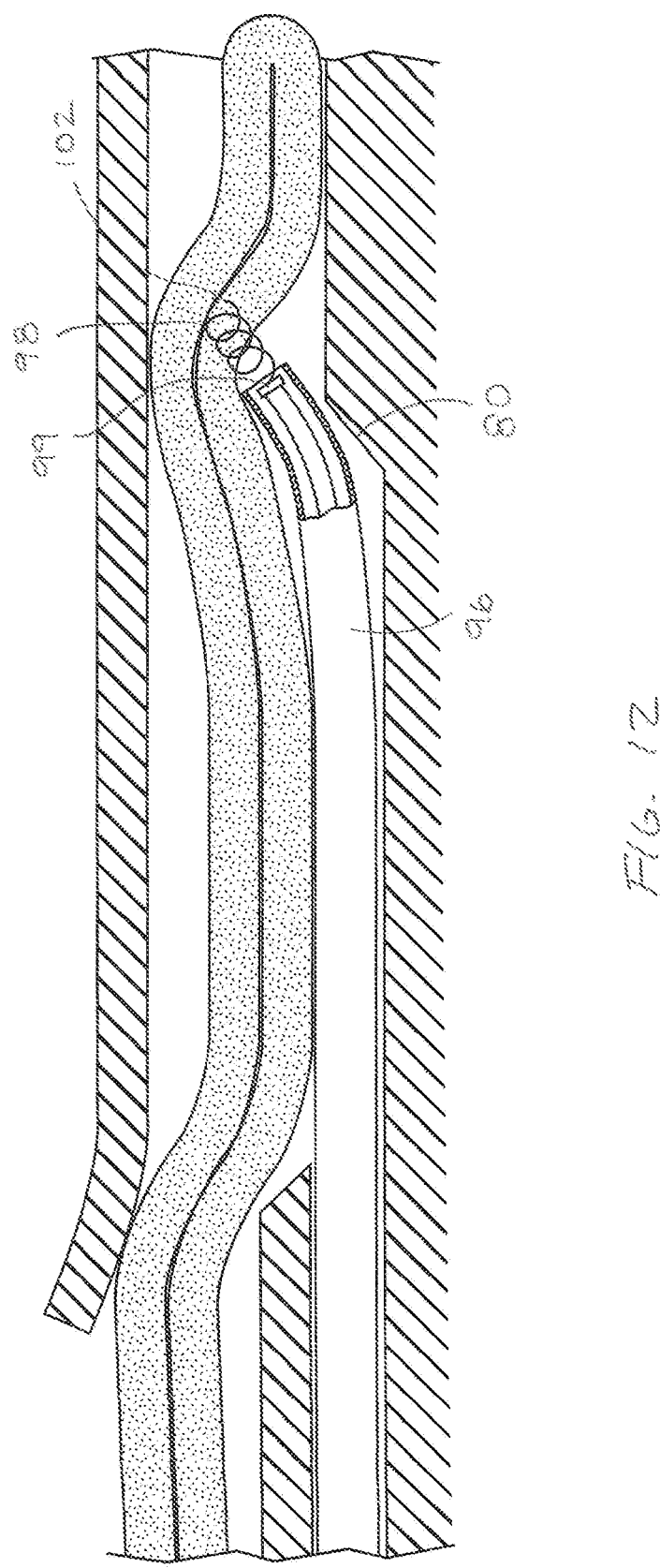
FIG. 12 shows another fastener applier.

Another fastener applier 96 is shown in FIG. 12. The fastener applier 96 contains a helical fastener 98 which is rotated into engagement with tissue using an actuator 99. The fastener applier 96 has an open distal end 100 which is directed toward the tissue by the ramp 80 to further compress the tissue fold prior to application of the fastener 98.

The helical fastener 98 is rotated and advanced with the actuator 99 so that a sharp tip 102 penetrates and advances into the tissue fold. After application of the helical fastener 98, another fastener applier 96 is used or another fastener 98 is delivered down the same applier 96.

Referring to FIGS. 13A and 13B, yet another fastener applier 101 is shown which delivers a helical fastener 103. The fastener 103 has a sharp tip 113 and form a number of coils 115 which define an axis 117. The fastener 103 is oriented longitudinally within a shaft 105 of the applier but is deployed in a manner which reorients the axis 117 upon deployment. An actuator 107 rotates and advances the helical fastener 103 which causes the helical fastener 103 to contact a deflecting element 109 which deflects the fastener 103 outwardly from the shaft 105 and into tissue. As the helical fastener 103 is deployed, the deflecting element 109 causes the axis 117 to be displaced at least 45 degrees from the stored position within the shaft to the deployed position outside the shaft 105.

Figure 14:
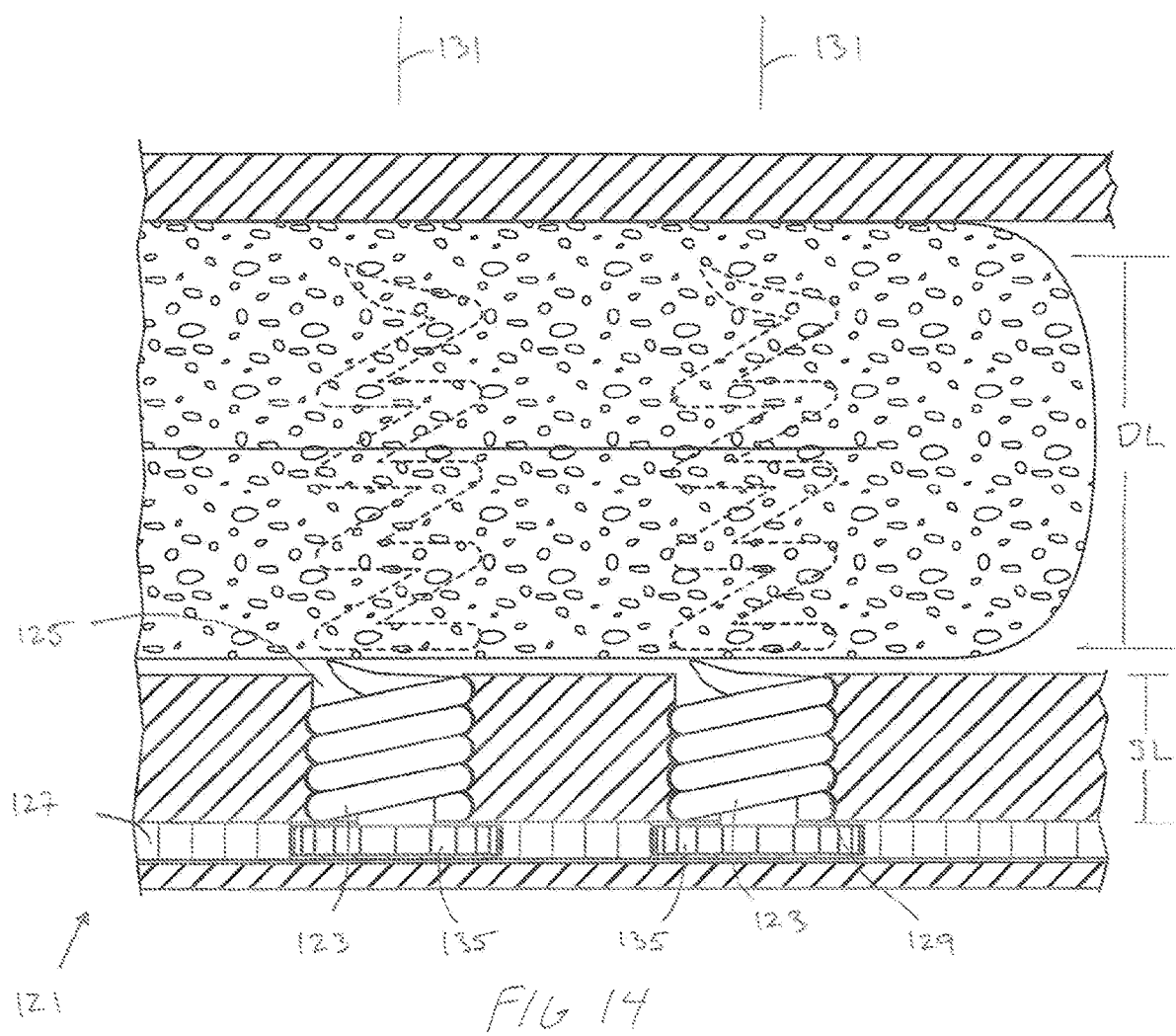
FIG. 14 shows still another fastener applier.

Referring to FIG. 14, still another fastener applier 121 is shown which delivers a plurality of helical fasteners 123. The fasteners can be delivered sequentially or simultaneously. The helical fasteners 123 forms a plurality of coils 129 which define an axis 131 and a length measured along the axis 131. The helical fasteners 123 are deployed through one or more side openings 125 upon movement of a rack 127 that rotates a gear 135 coupled to the fasteners 123 so that simple longitudinal motion of the rack 127 rotates all of the fasteners simultaneously. The fasteners 123 may be compressed in a stored position within the shaft 125 so that a natural unbiased length of the fastener 123 is at least 1.5 times, or even 2.0 times, a stored length (or compressed length) SL of the fasteners 123 within the shaft. As the fastener 123 is deployed, the fastener 123 naturally expands toward the natural unbiased length. In another aspect, the opening 125 may be oriented to direct the fastener 123 into an even larger length than the unbiased length by simply applying a greater pitch upon delivery through the opening. In this manner, the coils 129 are initially expanded so that tissue between the coils is compressed as the fastener 123 is deployed. For example, the fastener applier 121 may be configured to deploy the fastener 123 at a deployed length DL which is 2.5 times the stored length SL while the relaxed or unbiased length is 2.0 times larger than the stored or compressed length SL.

Methods of using the device 2 are now described. As will be appreciated, the present invention provides great flexibility in the manner in which the fold of tissue is formed and fastened together. As such, all methods of forming the fold shall be applicable to all methods of fastening the tissue together and such combinations are expressly included as part of the present invention even if not expressly described. Furthermore, all methods of manipulating tissue which are described in connection with moving tissue within or into the tissue shaper 4 may be practiced without the tissue shaper 4 or below the tissue shaper 4 and all such methods are expressly incorporated herein.

Figure 15:
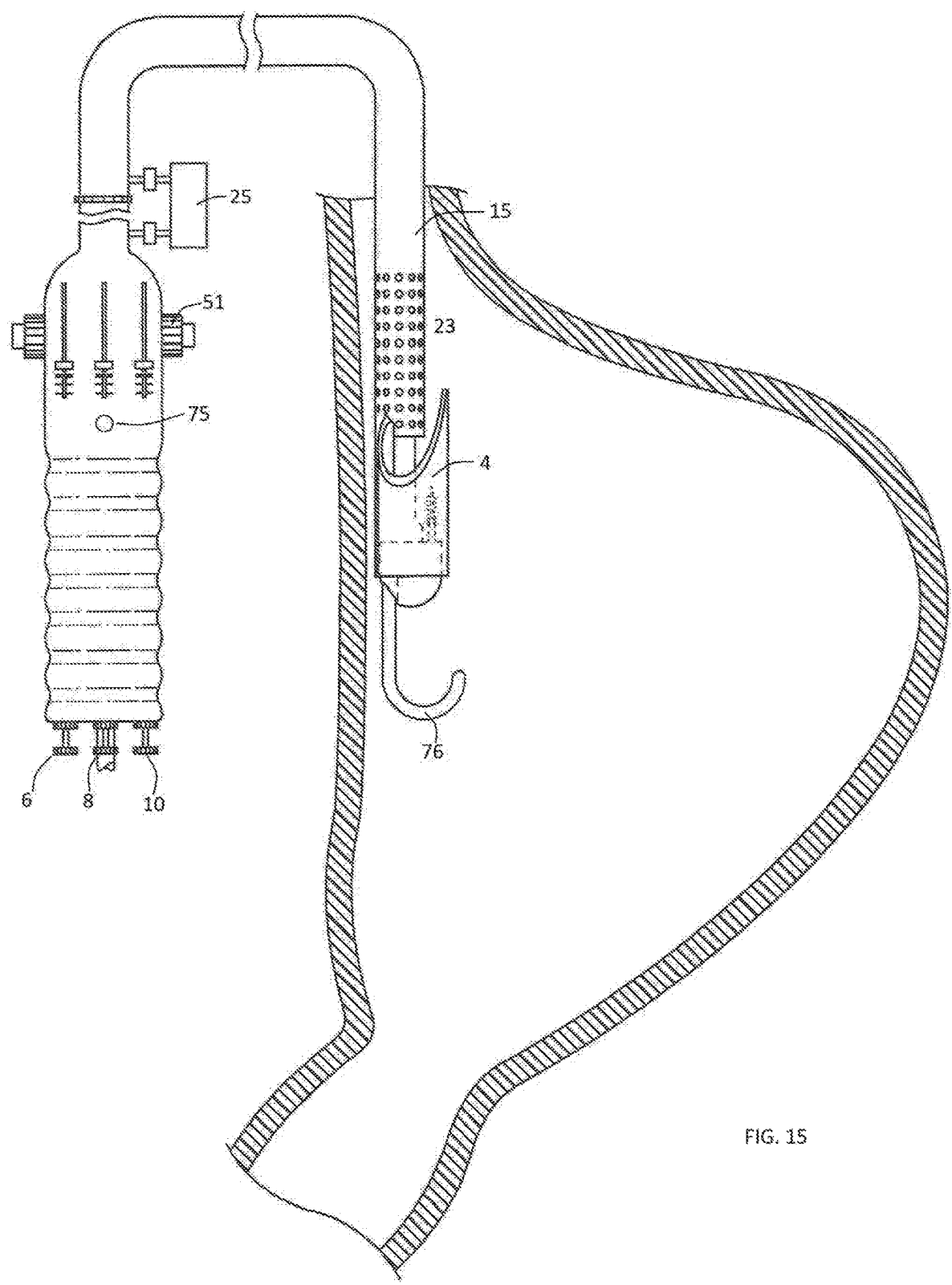
FIG. 15 shows the device delivered into the stomach and positioned in a desired location to recreate the intersection between the stomach and esophageal tract.

The device 2 is delivered down a patient's esophagus into the position of FIG. 15 so that the tissue shaper 4 is distal to the existing intersection between the esophageal tract and the stomach associated with a disease state. The visualization device 76 is used to view the stomach and orient the tissue shaper 4 within the stomach so that the tissue shaper 4 is positioned to create the fold of tissue in the desired position. An advantage of the present invention is that the user may not need to reposition the tissue shaper 4 once the desired position has been chosen. Of course, numerous aspects of the present invention may be practiced while moving the tissue shaper 4 between different positions without departing from the scope of the invention. For example, the tissue shaper 4 could be used to gather and fasten tissue into a fold and could be rotated to another position to create another fold.

At least one of the tissue displacing elements 6, 8, 10, such as the second tissue displacing element 8, is then extended outwardly to engage stomach tissue as shown in FIG. 3. The sheath 36 may be extended to cover the wire 35 to change the shape of the wire 35 to provide a different shape to facilitate engaging the desired stomach tissue location (see FIG. 7). The coil 32 is then rotated to engage the stomach tissue. Referring to FIGS. 1, 3 and 16, the second tissue displacing element 8 may then be pulled to draw stomach tissue toward the tissue shaper 4 which increases tension on the elongate element 34 and registers at the tension indicator 40. The user may refer to the tension indicator 40 to assist in assessing formation of the fold and the forces which may be required to maintain the fold. The user may retract the tissue displacing element 8 until a threshold tension is reached at which time the lock 42 is applied to maintain tension as shown in FIG. 17. The user may then engage stomach tissue with another of the elements 6, 10, such as the first element 6, and retract tissue until another threshold tension is reached, or desired displacement is achieved, and the appropriate lock 42 is applied as shown in FIG. 18. This process may be repeated until the stomach tissue has been displaced a desired amount by each of the tissue displacing elements 6, 8, 10 (see FIGS. 19 and 20).

An advantage of the present invention is that a stepwise displacement of tissue is possible since the plurality of elements 6, 8, 10 permit one of the elements 6, 8, 10 to be disengaged from tissue while the other two elements 6, 8, 10 substantially maintain the shape of the previously displaced tissue. In this manner, one of the elements 6, 8, 10, such as the second element 8, may be disengaged, repositioned to engage stomach tissue and displaced again as shown in FIGS. 18 and 19. The displaced stomach tissue may also be held by the vacuum orifices 23 in the primary shaft 16 (FIG. 1), the vacuum orifices 72 in the platform 14 (FIG. 5) and/or the tissue shaper 4 in addition to, or as a substitute for, the first and third tissue displacing elements 6, 10 which hold the tissue in a displaced state of FIG. 18. During displacement of stomach tissue, the elements 6, 8, 10 may displace the tissue by simply applying tension to the wire 35 and/or moving them within the slots 44 (FIGS. 5 and 6). For example, the first tissue displacing element 6 may be retracted until the coil 32 is proximate to the platform 14 followed by movement within the slot 44 to change the angular orientation as described herein.

Figure 21:
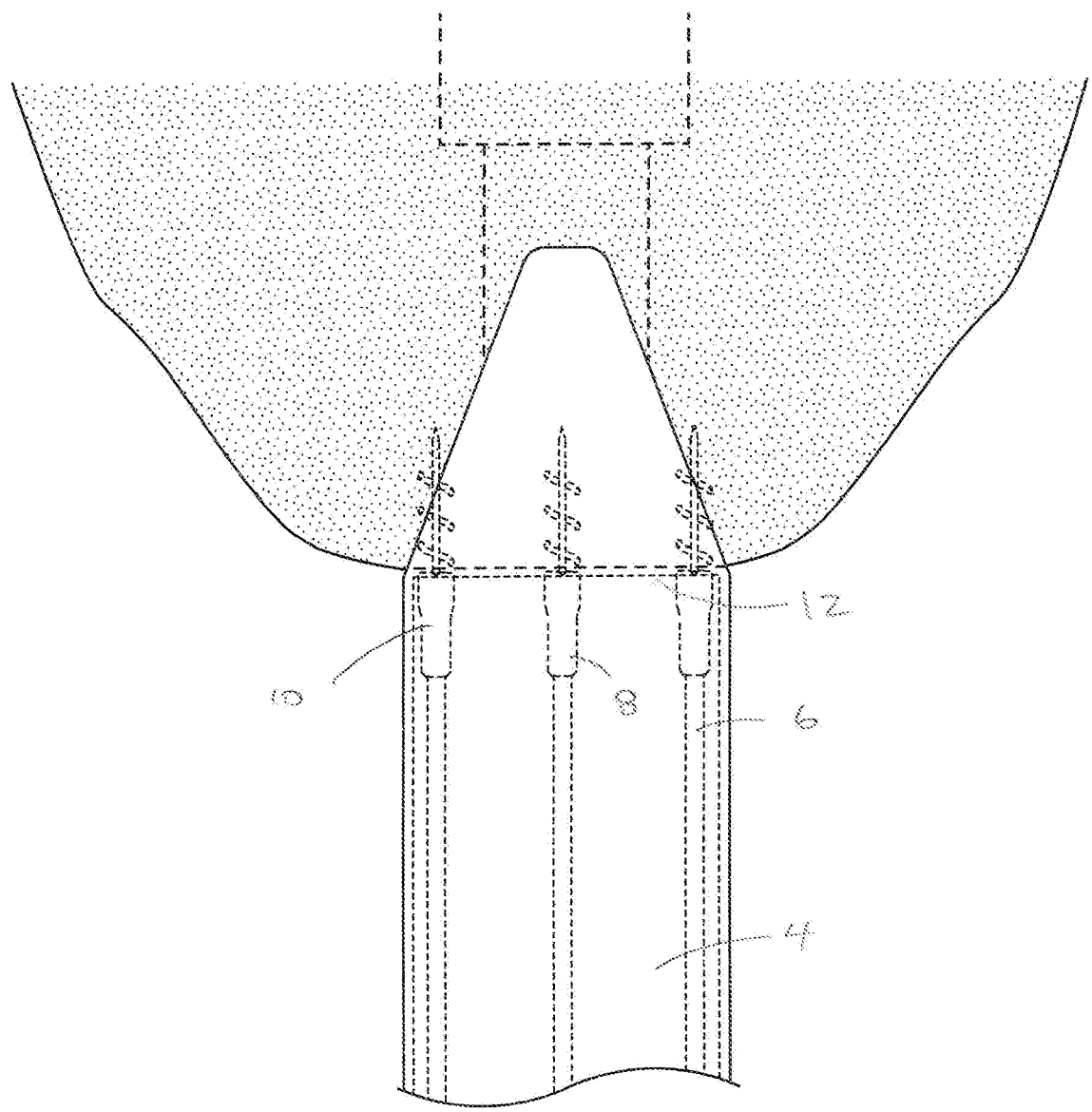
FIG. 21 shows all three tissue displacing elements engaged with tissue and retracted to the common retractor.
Figure 22:
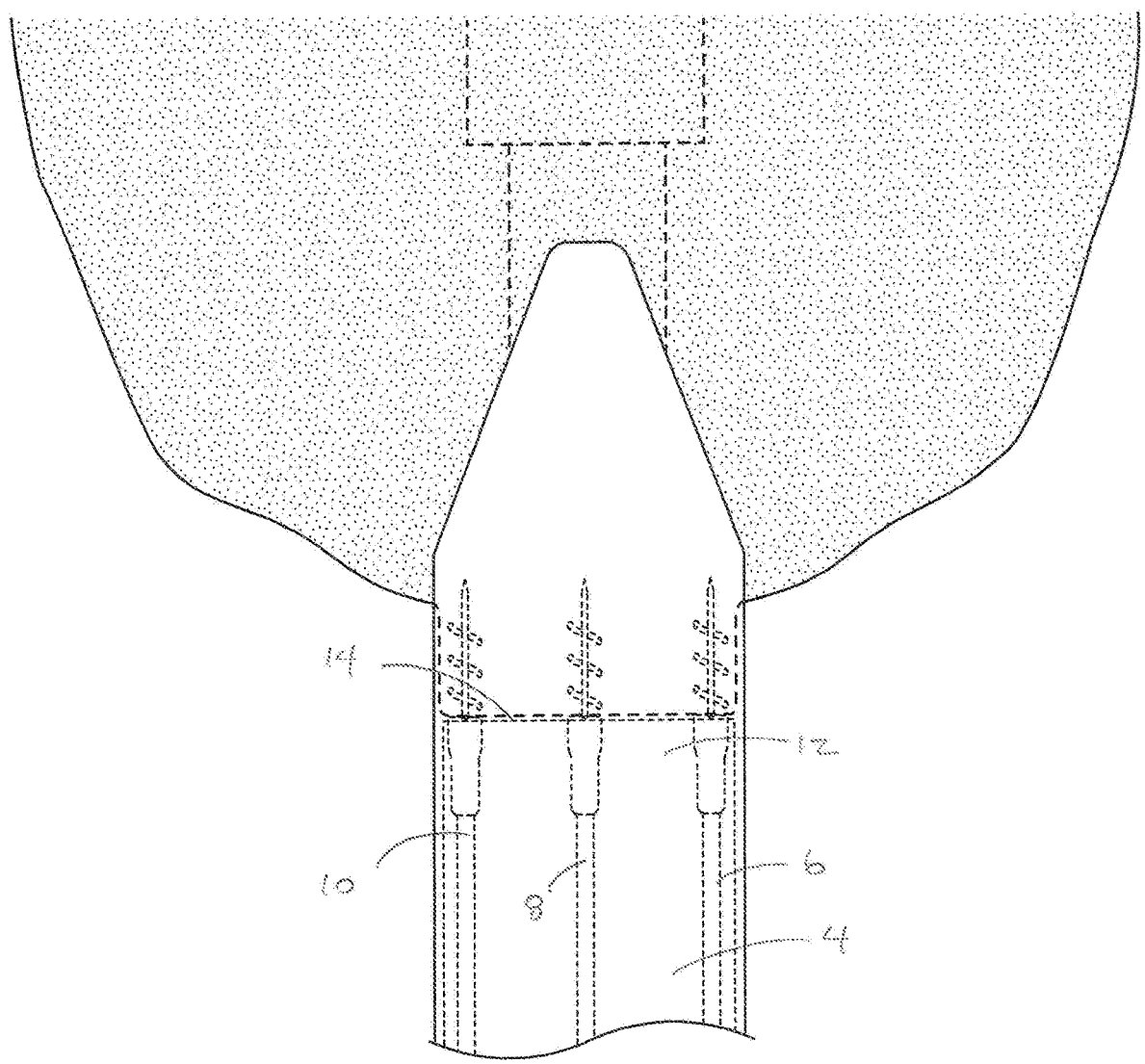
FIG. 22 shows three tissue displacing elements simultaneously displaced into the tissue shaper using the common retractor.
Figure 23:
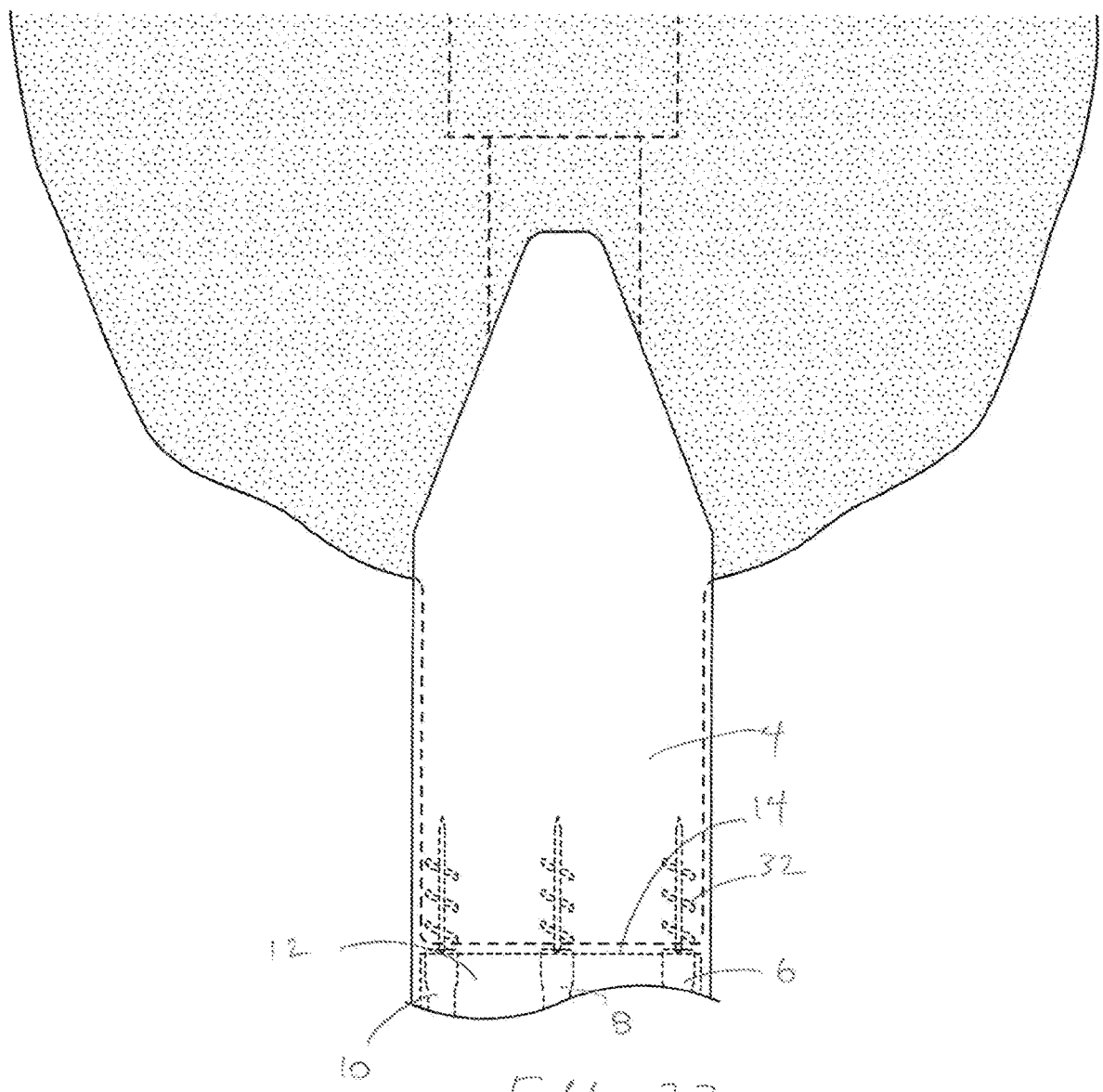
FIG. 23 shows all three tissue displacing elements retracted further by the common retractor.

Once the user has engaged tissue with each of the tissue displacing elements 6, 8, 10 and displaced each of the tissue displacing elements 6, 8, 10 as desired, the user may simultaneously displace all of the tissue displacing elements 6, 8, 10 using the common retractor 12 (see FIG. 21) to draw all three tissue displacing elements 6, 8, 10 into the tissue shaper 4 (see FIGS. 22 and 23). Suction may be applied to the orifices 72 in the platform 14 (FIG. 5) which may assist in drawing the tissue into the tissue shaper 4 as the common retractor 12 is moved into the tissue shaper 4. Of course, the tissue displacing elements 6, 8, 10 may be used to individually draw tissue into the tissue shaper 4, rather than using the common retractor 12 to simultaneously move all tissue displacing elements 6, 8, 10, without departing from the present invention. This may be accomplished by simply positioning the platform 14 in the cavity or even distal to the shaper 4 so that tissue is drawn into the tissue shaper 4 by the tissue displacing elements 6, 8, 10 alone (see FIG. 31).

Referring again to FIG. 8, the fold of tissue is shown contained within the tissue shaper 4. The fold of tissue forms the intersection between the esophageal tract and the stomach and has an esophageal side 131 and a stomach side 133 although at least some of the tissue on the esophageal side 131 may be characterized as stomach tissue prior to creation of the fold due to the disease state as described above. The tissue shaper 4 is sized to hold the fold of tissue and may be adapted to expand to a larger volume to accommodate the fold tissue due to the elastomeric portion 52 and the slits 60 (FIG. 4). Once the tissue is contained within the tissue shaper 4, the fold may be manipulated as now described or any other manner described herein.

The fold of tissue in the shaper 4 may be manipulated using the tissue shifting element 110 as shown in FIGS. 8-10. The needle 112 and/or needle 112A pierce one or both layers of the tissue fold and the wire 114 is then pulled proximally thereby moving the needles 112 downward to draw more tissue into the tissue shaper 4 and shift tissue downward within the shaper 4. The tissue shifting element 110 may also change a position of the intersection between the stomach and the esophageal tract to increase a length of the esophageal tract. When only one tissue layer is engaged as shown in FIG. 9, the tissue shifting element 110 displaces only the stomach side 133 of the fold while the esophageal side 131 is held stationary by the vacuum orifices 23 on the primary shaft 15 (see FIG. 1). The tissue may also be shifted within the tissue shaper 4 using the elements 6, 8, 10. In this manner, the tissue displacing elements 6, 8, 10 serve as tissue shifting elements in accordance with the present invention. For example, the tissue displacing elements 6, 8, 10 may be used to displace the tissue further into the cavity 50 or through the open distal end 65 of the tissue shaper 4 (see FIG. 31). The tissue displacing elements 6, 8, 10 may also be moved within the slots 44 to shift and displace tissue within the tissue shaper 4 in any manner described herein. The tissue displacing elements 6, 8, 10 may all be used to apply longitudinal displacement as well as a change in angular position relative to the longitudinal axis similar to use of the slots 44.

Figure 24:
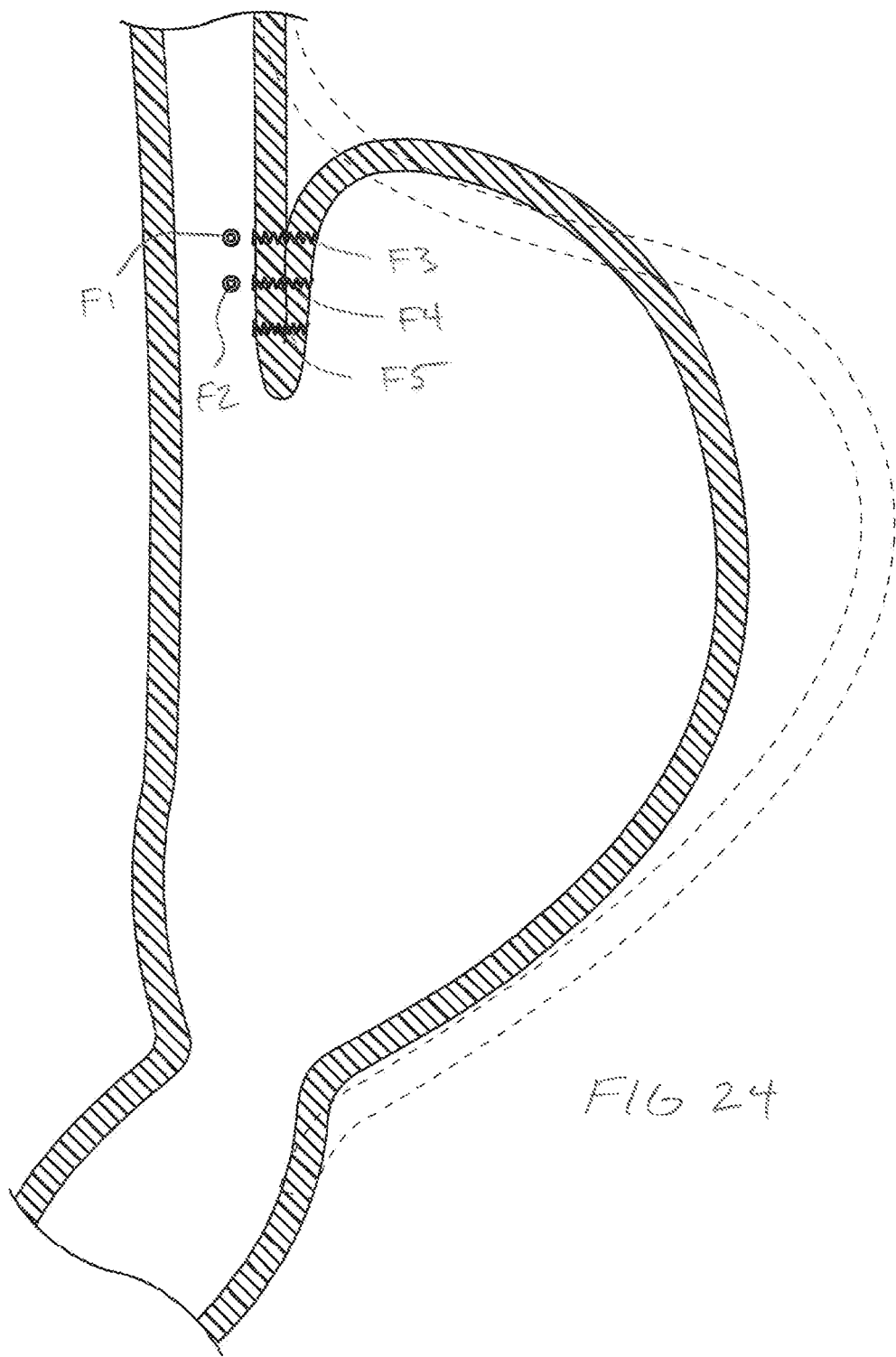
FIG. 24 shows fasteners applied to the stomach to create a tissue fold in accordance with the present invention.
Figure 25:
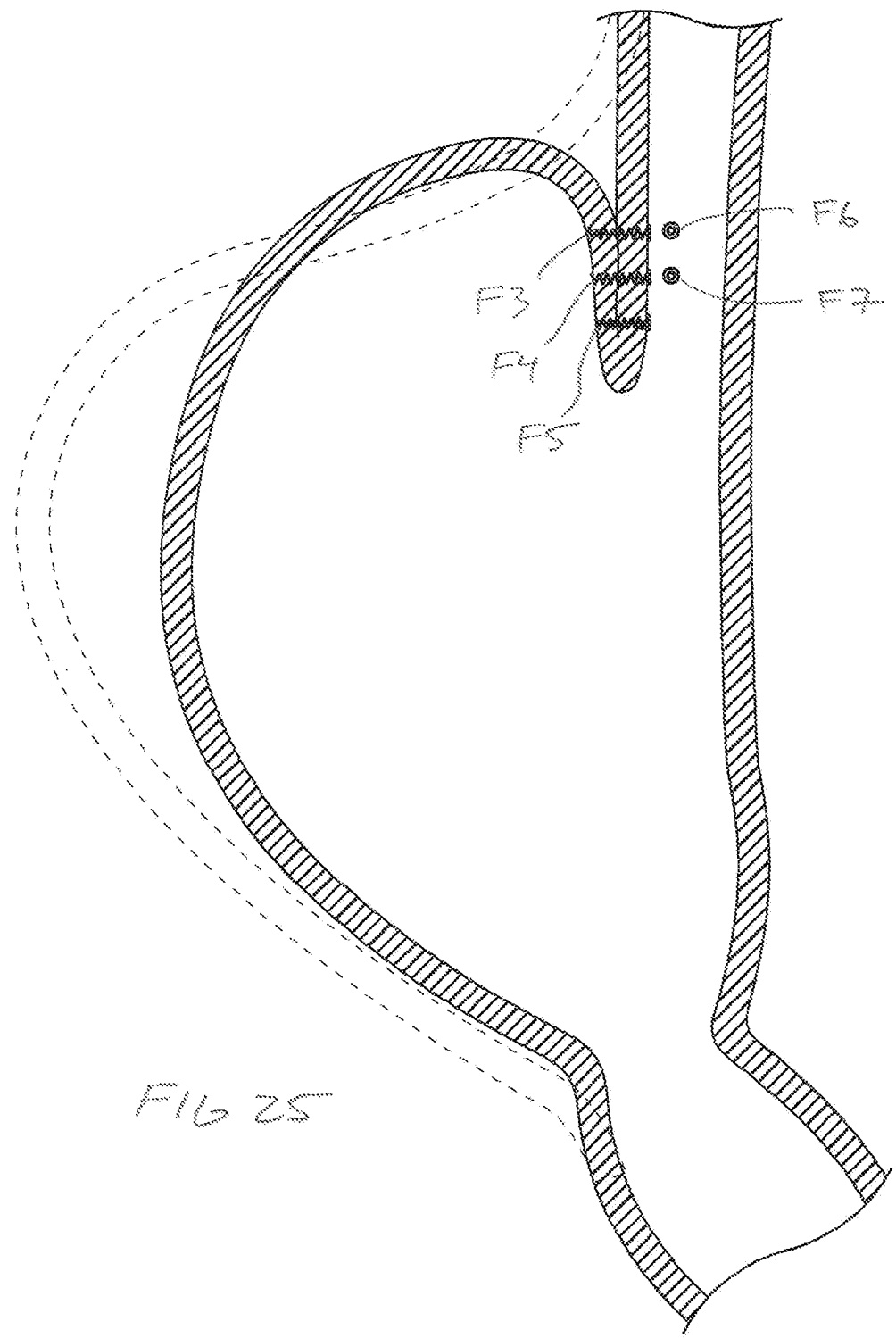
FIG. 25 show another view of the stomach where additional fasteners have been applied to the tissue fold.

Methods of fastening the fold of tissue together and additional methods of manipulating the tissue are now described. Each of the fastening methods may be used with any of the methods of manipulating tissue and forming the fold described herein. For the purpose of describing these methods, fasteners F1, F2, F3, F4, F5, F6, F7 are shown in FIGS. 24 and 25. Fasteners F1, F2 are longitudinally aligned at one end of the tissue fold (formed near the end 24 of the tissue shaper 4) and F6, F7 are at the other end of the tissue fold (and formed near the other end 26 of the tissue shaper 4). Fasteners F3-F5 are longitudinally aligned along a central portion of the fold of tissue. Of course, more or fewer fasteners may be applied and any of the fastener appliers described herein or any other suitable fastener applier may be used with or integrated with the device 2. As mentioned above, the clamping elements 61, 63 may be used to clamp the fold of tissue during application of fasteners and all methods described herein may include application of the clamping elements 61, 63 during each fastening step. The clamping elements 61, 63 may be released if further tissue displacing steps are carried out followed by application of the clamping elements 61, 63 before applying another fastener.

In one aspect of the present invention, the fastener applier 90 of FIG. 11 is used to deliver a plurality of fasteners, such as the staples 94, simultaneously. Once the fold of tissue is held in the desired shape, as shown in FIG. 23 for example, the fasteners F1, F2 may be applied simultaneously with the fastener applier 90 positioned at position P1 of FIG. 6. Fasteners F3, F4, F5 are applied at position P2 and fasteners F6, F7 are applied at position P3. Three separate fastening appliers 90 may be used to simultaneously apply each row of fasteners or one fastener applier 90 may be used to apply all of the fasteners in three separate steps using different preselected cartridges 92, 92A, 92B. When only one fastener applier 90 is used, the fastener cartridge 92 may be changed after each row of fasteners is applied. If the fastener applier has enough fasteners, the fastener applier 90 is simply rotated within the window 80 to the next appropriate location and the next set of fasteners 94 is applied. The fastener cartridge may be adapted to dispense the necessary amount of fasteners 94 at each application.

The fasteners 1-7 may be applied after all tissue manipulations have been completed. Alternatively, some of the fasteners F1-F7 may be applied and the tissue is further manipulated with the elements 6, 8, 10 or shifting element 110 followed by application of more fasteners F1-F7. This process may be repeated until all of the fasteners F1-F7 are applied while the user manipulates tissue between each fastening step as desired. The vacuum orifices 23 in the shaft 15 or the vacuum orifices 72 in the platform 14 may be used to further stabilize the fold of tissue between the fastening steps. The tissue shaper 4 itself may also help to firmly hold the fold of tissue (particularly if the elastomeric portion 52 is used) yet still permits shifting of tissue within the tissue shaper 4 and still permits tissue to be drawn into the tissue shaper 4. Various methods of manipulating tissue with the device 2 may include holding selected parts of the tissue fold stationary while tissue is manipulated with another part of the device 2. To this end, the vacuum orifices 23 in the shaft 15, the vacuum orifices 72 in the common retractor 23, the tissue displacing elements 6, 8, 10 and even the tissue shifting elements 110 may be used to hold parts of the tissue stationary while other parts of the device 2 are used to further displace the tissue in any manner described herein.

Figure 26:
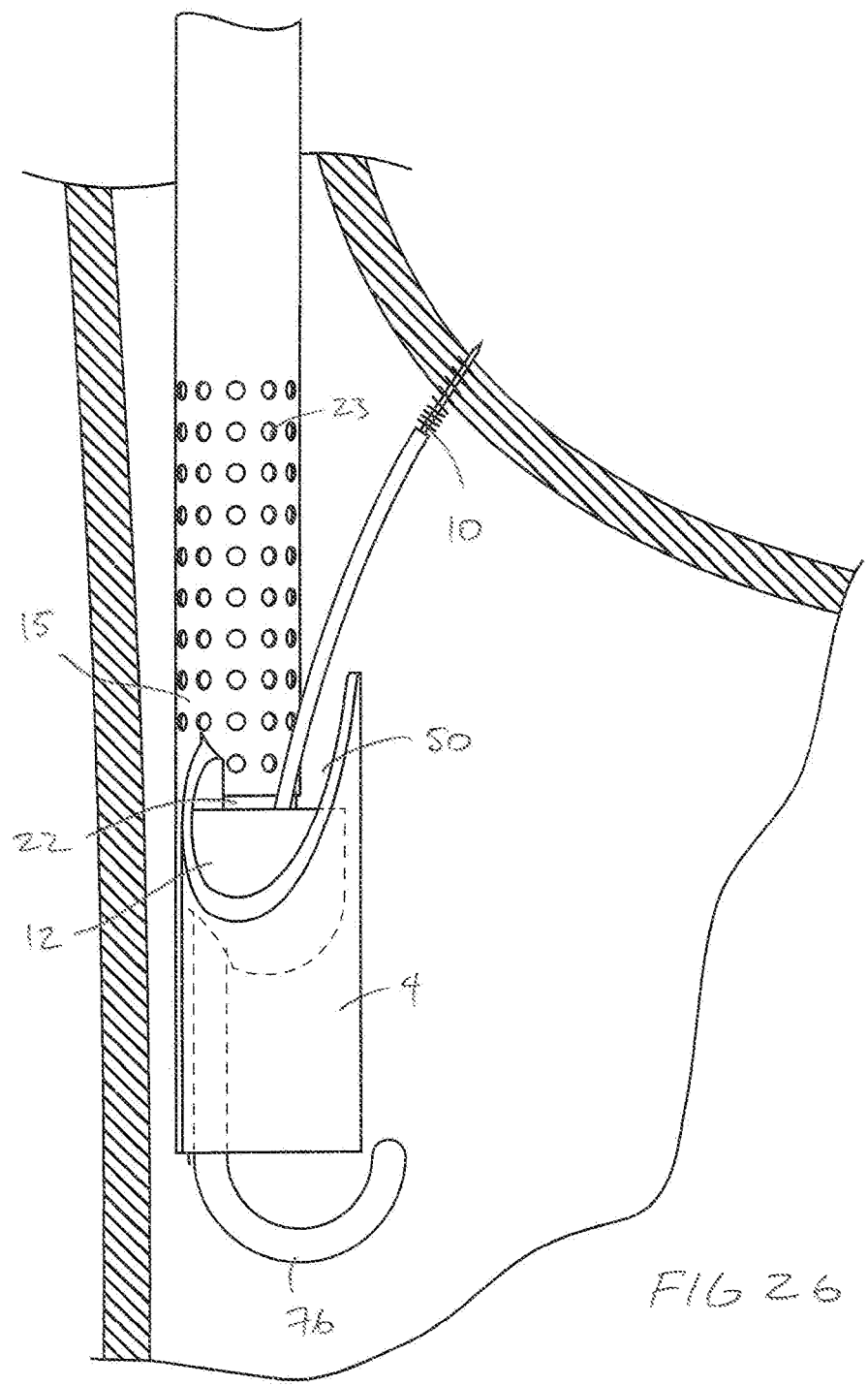
FIG. 26 shows the tissue displacing element engaged with stomach tissue.

In one example of a procedure having a number of fastening and tissue manipulation steps, fasteners 1, 2 and fasteners 6, 7 at the ends 24, 26 of the tissue shaper 4 are applied first followed by application of fasteners 3, 4, 5 along the central portion of the tissue shaper 4. In this manner, the tissue fold is created at the ends 24, 26 of the tissue shaper 4 first followed by formation of the central portion of the fold. Referring to FIGS. 26-28, the third tissue displacing elements 10 (and the first tissue displacing element 6 in similar fashion on the opposite side) extends outwardly to provide for longitudinal and an angular displacement upon retraction as described herein. The first and third tissue displacing elements 6, 10 may also be manipulated within the slots 44, such as toward the ends 24, 26 of the tissue shaper 4, as shown in FIGS. 27-28. In this manner, tissue has been drawn towards the ends 24, 26 of the tissue shaper 4. The tissue is the drawn into the shaper 4 by moving the first and third displacing elements in any manner described herein to the dotted line position of FIG. 28. The fasteners 1, 2 and 6, 7 may then be applied near the ends 24, 26 of the tissue shaper 4.

Figure 29:
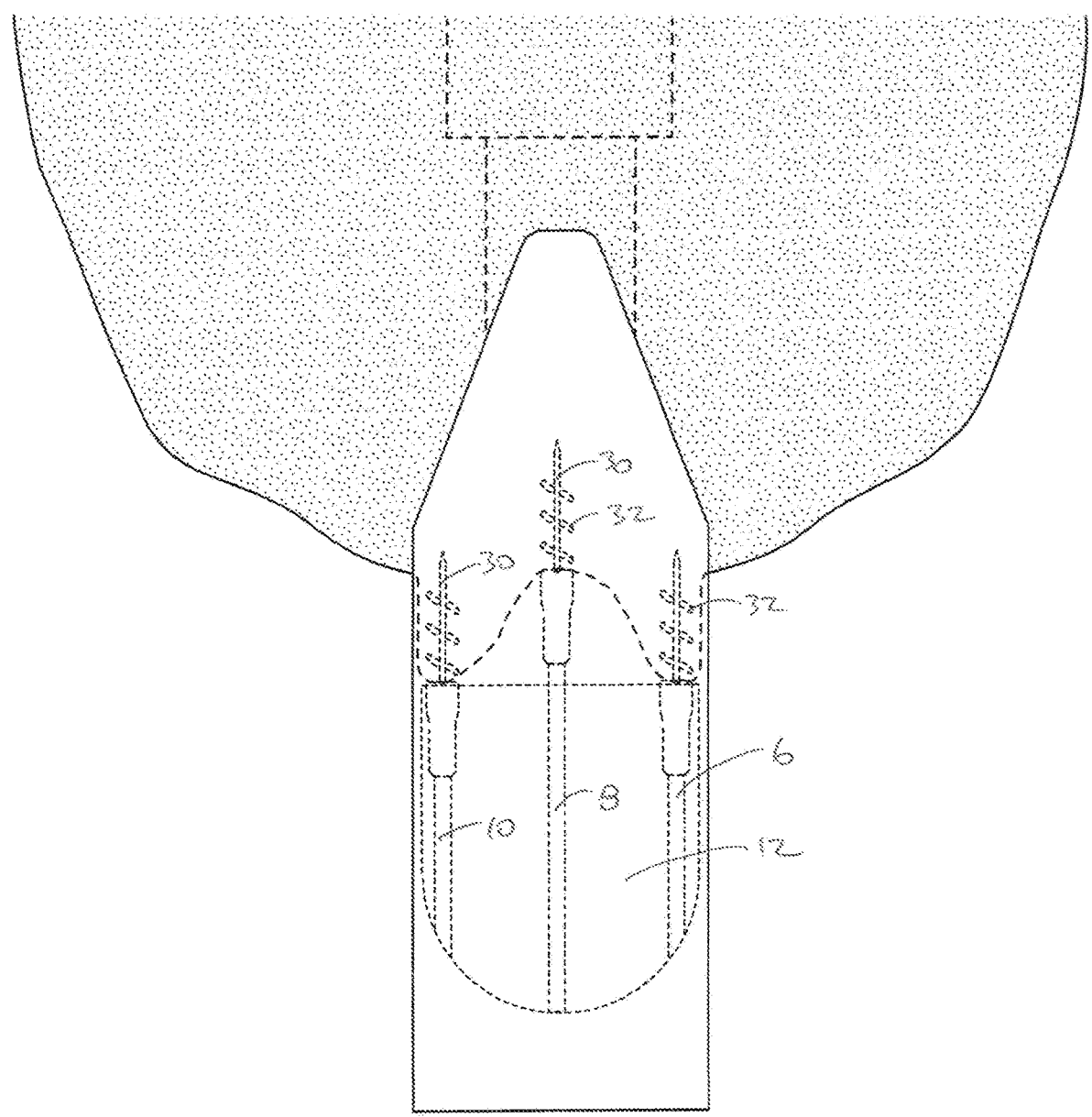
FIG. 29 shows the second tissue displacing element engaged with tissue after displacement in accordance with FIGS. 26, 27, 28A and 28B

The second tissue displacing element 8 may then be used to engage stomach tissue in the central portion of the tissue shaper 4 as shown in FIG. 29. The tissue is then pulled down by the second tissue displacing element 8 and fasteners 3, 4, 5 may then be applied simultaneously or may be applied one at a time between manipulations of the second tissue displacing element 8. When moving the first and third tissue displacing elements 6, 10, the lock 75 may be used to lock the first and third tissue displacing elements together 6, 10 and simultaneously move the first and third tissue displacing elements 6, 10.

Figure 30:
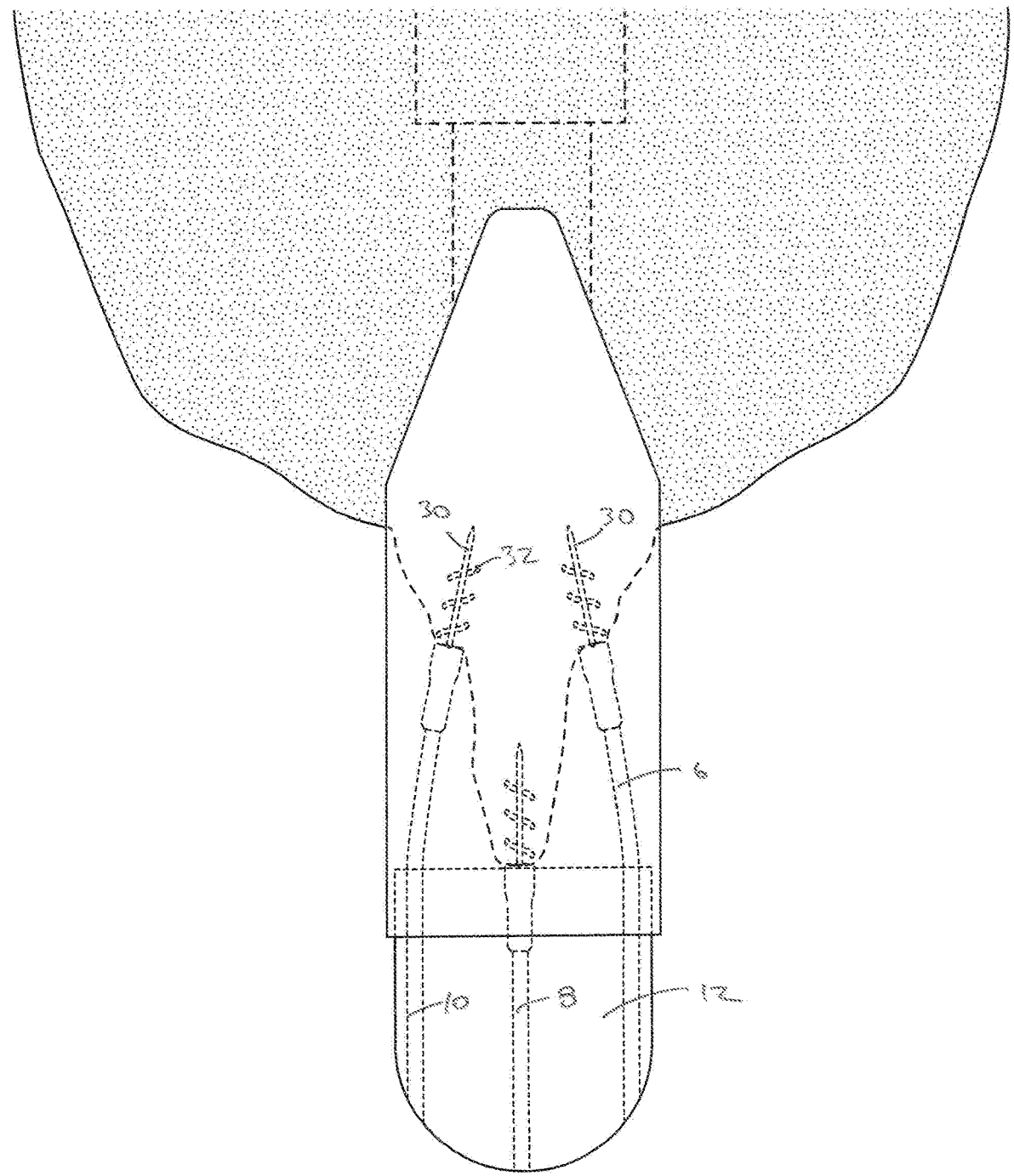
FIG. 30 shows the second tissue displacing element moving tissue with the first and third tissue displacing elements prior to displacement towards the ends of the shaper.

In another example of the present invention, fasteners 3, 4, 5 along the middle of the tissue shaper 4 (and along the middle of the tissue fold being created) are applied first and tissue is then manipulated prior to application of fasteners 1,2 and 6, 7 at the ends 24, 26 of the tissue shaper 4. Tissue may be manipulated between fastening steps by engaging tissue with the first and third tissue displacing elements 6, 10 and/or tissue shifting element 110 to tighten or loosen the fold, to lengthen the ends of the fold or to longitudinally stretch the fold as deemed necessary and as described herein. For example, the second tissue displacing element 8 is used to displace the central portion of the tissue fold downward and the first and third tissue displacing elements 6, 10 may then be engaged with tissue as shown in FIG. 30. The first and third tissue displacing elements 6, 10 are then retracted to pull tissue downward and also to move tissue towards the ends of the tissue shaper 4. To this end, the tissue displacing elements 6, 10 may impart displacements in any manner described herein. For example, the first and third tissue displacing elements 6, 10 may pull tissue towards the ends 24, 26 of the mold followed by displacement within the slots 4 toward the ends 24, 26 in a manner similar to the displacements shown in FIGS. 26-28 but in the opposite direction. In this manner, the tissue fold is created from the central portion towards the ends 24, 26 of the tissue shaper 4.

In yet another method of applying the fasteners F1-F7, the fastener applier may be held in a substantially stationary position and the tissue is manipulated after each fastener application. Referring again to FIGS. 22 and 23, an example of such a method is shown. Fastener F3 is applied in the position of FIG. 22. The tissue is then pulled further into the tissue shaper 4 using the tissue displacing elements 6, 8, 10 (or the common retractor to displace all three tissue displacing elements 6, 8, 10 simultaneously) and fastener F4 is then applied without moving the fastener applier from the position in which fastener F3 was applied. In this manner, the fastener applier may stay in a single, stationary position for several fastening steps while the tissue is manipulated between fastening steps. Fastener F5 may then be applied after further displacement of tissue to complete a row of fasteners near the central plane. Rather than completing the row of fasteners, the user may rotate the fastener applier to apply fasteners F1 and/or F6.

Referring now to FIG. 31, the tissue may also be manipulated through the open end 65 of the tissue shaper 4 and all methods described above may be practiced in this manner. For example, the method of applying the fasteners F1-F7 just described may be useful when the fold of tissue extends through the open end 65 of the tissue shaper 4. The user may clearly see how the formation of the fold is progressing as each fastener F1-F7 is applied and the fold becomes exposed through the open end 65 of the tissue shaper 4. As such, all methods of manipulating and fastening tissue described herein shall be applicable to methods of gathering and fastening tissue which partially extends through the open end 65 of the tissue shaper 4.

The present invention has been described with respect to the preferred embodiment, however, it is understood that numerous modifications could be made without departing from the scope of the present invention. For example, the tissue shaper 4 may be omitted or could be a user actuated structure without departing from the scope of the present invention.

What is claimed is:

1. A medical device for forming an intersection between the esophagus and the stomach, comprising:
   a shaft and a plurality of vacuum orifices on the shaft for grasping esophageal tissue and a tissue displacing element coupled to the shaft, the shaft defining a longitudinal axis;
   a tissue shaper coupled to the shaft and having a tubular structure open at a first end and a second end and forming a fixed volume cavity that receives and forms a fold of stomach tissue displaced by the tissue displacing element, a tissue shifting element being configured to displace the fold of stomach tissue held by the tissue shaper;
   a flexible elongate element having a tissue engaging element at a distal end of the tissue displacing element; and
   a plurality of fasteners for insertion into the fold of stomach tissue.

2. The medical device of claim 1, wherein the tissue shaper is removably attached to the shaft.

3. The medical device of claim 2, wherein the tubular structure of the tissue shaper has an open side proximate the esophagus.

4. The medical device of claim 3, wherein the tissue shaper has a curved cross-sectional shape.

5. The medical device of claim 4, wherein the curved cross-sectional shape of the tissue shaper forms an arc of at least 180° relative to a longitudinal axis between the first end and the second end.

6. The medical device of claim 5, further comprising:
   a fastener lumen, a fastener applier being slidable within the fastener lumen to different longitudinal positions for insertion of the plurality of fasteners.

7. The medical device of claim 6, further comprising:
   the fastener lumen permitting reorientation of the fastener applier by at least 90 degrees relative to the longitudinal axis of the shaft.

8. The medical device of claim 5, further comprising:
   a fastener cartridge containing the plurality of fasteners.

* * * * *